US012653796B2

(12) United States Patent
Gautheron et al.

(10) Patent No.: US 12,653,796 B2
(45) Date of Patent: Jun. 16, 2026

(54) COMPOUNDS FOR USE (IN PARTICULAR RIPA-56) IN THE PREVENTION AND/OR TREATMENT OF NON-ALCOHOLIC FATTY LIVER DISEASE

(71) Applicants: SORBONNE UNIVERSITE, Paris (FR); INSTITUT NATIONAL DE LA SANTÉ ET DE LA RECHERCHE MEDICALE (INSERM), Paris (FR); ASSISTANCE PUBLIQUE—HOPITAUX DE PARIS, Paris (FR)

(72) Inventors: Jérémie Gautheron, Alfortville (FR); Vlad Ratziu, Servon (FR)

(73) Assignees: SORBONNE UNIVERSITE, Paris (FR); INSTITUT NATIONAL DE LA SANTÉ ET DE LA RECHERCHE MEDICALE (INSERM), Paris (FR); ASSISTANCE PUBLIQUE - HOPITAUX DE PARIS, Paris (FR)

( * ) Notice: Subject to any disclaimer, the term of this patent is extended or adjusted under 35 U.S.C. 154(b) by 1088 days.

(21) Appl. No.: 17/642,905

(22) PCT Filed: Oct. 23, 2020

(86) PCT No.: PCT/EP2020/079932
§ 371 (c)(1),
(2) Date: Mar. 14, 2022

(87) PCT Pub. No.: WO2021/078958
PCT Pub. Date: Apr. 29, 2021

(65) Prior Publication Data

US 2022/0362179 A1 Nov. 17, 2022

(30) Foreign Application Priority Data

Oct. 24, 2019 (EP) .................................... 19306380

(51) Int. Cl.
*A61K 31/165* (2006.01)
*A61P 1/16* (2006.01)

(52) U.S. Cl.
CPC .............. *A61K 31/165* (2013.01); *A61P 1/16* (2018.01)

(58) Field of Classification Search
CPC ................................ A61K 31/165; A61P 1/16
See application file for complete search history.

(56) References Cited

FOREIGN PATENT DOCUMENTS

| | | | |
|---|---|---|---|
| WO | 2016/101885 | A1 | 6/2016 |
| WO | 2018/064373 | A1 | 4/2018 |
| WO | 2018/192416 | A1 | 10/2018 |

OTHER PUBLICATIONS

Ren, Y., et al., "Discovery of a Highly Potent, Selective, and Metabolically Stable Inhibitor of Receptor-Interacting Protein 1 (RIP1) for the Treatment of Systemic Inflammatory Response Syndrome," Journal of Medicinal Chemistry 60 (3):972-986, Feb. 9, 2017.

Hardy, T., et al., "Nonalcoholic Fatty Liver Disease: New Treatments," Current Opinion in Gastroenterology, 31(3):175-186, May 1, 2015.

Majdi, A., et al., "Inhibition of Receptor-Interacting Protein Kinase 1 Improves Experimental Non-Alcoholic Fatty Liver Disease," Journal of Hepatology 72(4):627-635, Nov. 21, 2020.

International Search Report mailed Jan. 18, 2021, issued in corresponding International Patent Application No. PCT/EP2020/079932, filed Oct. 23, 2020, 4 pages.

Written Opinion mailed Jan. 18, 2021, issued in corresponding International Patent Application No. PCT/EP2020/079932, filed Oct. 23, 2020, 6 pages.

*Primary Examiner* — Kevin E Weddington
(74) *Attorney, Agent, or Firm* — CHRISTENSEN O'CONNOR JOHNSON KINDNESS PLLC

(57) ABSTRACT

The present invention relates to compounds and compositions comprising said compounds, for use in the prevention and/or treatment of non-alcoholic fatty liver disease (NAFLD), in particular hepatic steatosis or non-alcoholic steatohepatitis (NASH).

8 Claims, 17 Drawing Sheets

Figure 1:
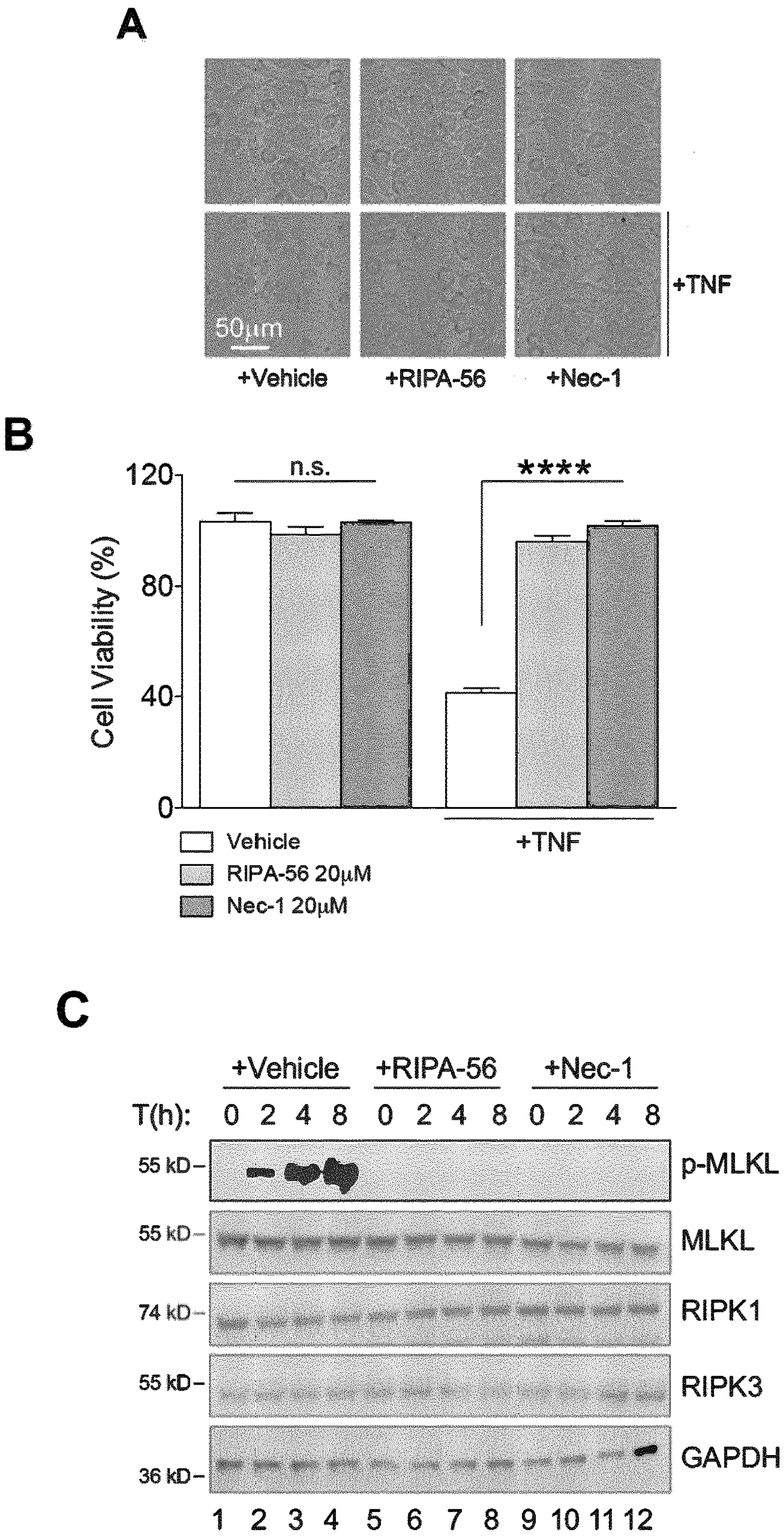

COMPOUNDS FOR USE (IN PARTICULAR RIPA-56) IN THE PREVENTION AND/OR TREATMENT OF NON-ALCOHOLIC FATTY LIVER DISEASE

The present invention relates to compounds and compositions comprising said compounds, for use in the prevention and/or treatment of non-alcoholic fatty liver disease (NAFLD), in particular hepatic steatosis or non-alcoholic steatohepatitis (NASH).

Non-alcoholic fatty liver disease (NAFLD), which has been paralleling the worldwide increase in obesity, has become the most common chronic liver disease, and now affects up to one third of the adult population in Western countries. This entity encompasses both hepatic steatosis and steatohepatitis. The hepatic steatosis is the abnormal retention of lipids in liver. It reflects an impairment of the normal processes of synthesis and elimination of triglyceride fat. In contrast to steatosis, where intracellular storage of fat does not drive mechanisms of lipotoxicity or organ damage, steatohepatitis can progress to cirrhosis and ultimately end-stage liver disease, therefore carrying most of the liver-related morbidity and mortality associated with NAFLD. The distinction between hepatic steatosis and steatohepatitis is defined morphologically based on the presence of lobular or portal inflammation and hepatocellular injury, yet little is known about the mechanistic determinants of cell injury and death in steatohepatitis.

Hepatocyte cell death is a critical event in the progression of all chronic inflammatory liver diseases. Until recently, two main forms of cell death were recognized: apoptosis, which occurs in a highly controlled manner, and necrosis that is accidentally triggered. However, during the past few years, it became clear that programmed cell death was not restricted to apoptosis, and comprised other forms of regulated cell death. Necroptosis is one of them, combining the molecular machinery of the extrinsic apoptotic pathways with an execution similar to necrosis, that involves oncosis, organelle dilatation and plasma membrane disruption. Unlike apoptosis that requires the activation of aspartate-specific proteases known as caspases, necroptosis is driven by the activation of the receptor-interacting protein kinase (RIPK) 1 and 3, and the pseudo kinase mixed lineage kinase domain-like (MLKL). When activated, RIPK1, RIPK3 and MLKL form the necrosome. Unlike apoptosis, a generally silent mode of cell death, necroptosis can lead to massive inflammation via the release of damage-associated molecular patterns (DAMPs), and the activation of the necrosome-dependent inflammasome, which triggers the maturation of pro-IL-1β and pro-IL-18, two highly pro-inflammatory cytokines.

Findings in previous preclinical and clinical studies indicated that the prevention of apoptosis through pan-caspase inhibitors was able to reduce liver injury in NASH, although to a limited extent, suggesting that other modes of cell death are likely involved. Moreover, in the presence of a pan-caspase inhibitor, the stimulation of a death receptor causes the preferential activation of necroptosis. Therefore, caspase inhibition can induce necroptosis and thereby could actually favor ongoing injury in NASH. It was also demonstrated that necroptosis was activated in the hepatocytes of patients with NASH (Gautheron et al., EMBO Mol Med 2014; 6:1062-1074).

There thus remains a genuine need for an effective prevention or treatment of NAFLD, in particular of hepatic steatosis or NASH.

The present invention is believed to meet such need by providing compounds and compositions for preventing and/or treating NAFLD.

Surprisingly, the Inventors have observed that RIPA-56, a highly specific inhibitor of RIPK1, has positive effects to reduce steatosis, inflammation and fibrosis of the liver.

In this context, the present invention concerns a compound of formula (I):

(I)

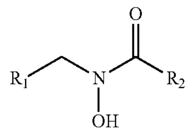

wherein:

$R_1$ is phenyl, optionally fluorinated or methylated, $R_2$ is 1,1-dimethylpropyl, optionally fluorinated, or a pharmaceutically acceptable salt or hydrate thereof, for use in the prevention and/or treatment of NAFLD, in particular non-alcoholic hepatic steatosis or NASH.

The present invention further relates to a composition comprising at least one compound as defined above as active ingredient and at least one pharmaceutically acceptable excipient, for use in the prevention and/or treatment of NAFLD, in particular non-alcoholic hepatic steatosis or NASH.

The present invention further relates to a method for preventing and/or treating NAFLD, in particular non-alcoholic hepatic steatosis or NASH, by means of administration, to a patient in need thereof, of an effective amount of a compound as defined above.

The present invention further relates to the use of a compound as defined above for the manufacture of a medication for preventing and/or treating NAFLD, in particular non-alcoholic hepatic steatosis or NASH.

In the present invention, "pharmaceutically acceptable" is intended to mean that which is useful in the preparation of a pharmaceutical composition, generally safe, nontoxic and neither biologically nor otherwise undesirable and acceptable for both veterinary and human pharmaceutical use.

"Pharmaceutically acceptable salt" of a compound is intended to mean a salt that is pharmaceutically acceptable, as defined herein, and that has the desired pharmacological activity of the parent compound. Pharmaceutically acceptable salts include salts of the active compound which are prepared with relatively nontoxic acids or bases.

The compound of the invention can exist in unsolvated forms as well as solvated forms, including hydrated forms. In general, the solvated forms are equivalent to unsolvated forms and are intended to be encompassed within the scope of the invention. In general, all physical forms are equivalent for the uses contemplated by the invention and are intended to be within the scope of the invention.

By "pharmaceutically acceptable excipient" is meant, according to the invention, a non-pharmaceutically active additive used in the manufacture of a pharmaceutical composition, which allows the pharmaceutically active ingredient to be manufactured into a pharmaceutical formulation or a galenic formulation providing the necessary bioavailability of the medicament to the patient upon the administration of the pharmaceutical composition. The excipient is preferably compatible with the other ingredients of the composition and produces no adverse effect, allergic reaction or other undesirable reaction when it is administered to a human or an animal.

In the present invention, the term "non-alcoholic fatty liver disease" or "NAFLD" designates a condition in which excess fat is stored in liver. This buildup of fat is not caused by heavy alcohol use. Inside the spectrum of NAFLD, there are entities going from simple hepatic steatosis to nonalcoholic steatohepatitis (NASH).

In the present invention, the term "hepatic steatosis", also called "simple fatty liver", refers to a form of NAFLD wherein there is an abnormal accumulation of fat by the liver which can cause complications in cases of obesity, type 2 diabetes or other components of the metabolic syndrome.

In the present invention, the term "non-alcoholic steatohepatitis" (NASH)" refers to a form of NAFLD where steatosis coexists with hepatic inflammation and hepatic cell injury. Inflammation and liver cell damage can cause fibrosis, or scarring, of the liver. NASH may lead to cirrhosis or liver cancer.

By "treatment" is meant, according to the present invention, the decrease or the disappearance a disease, a disorder or one or more signs and/or symptoms. In particular, the treatment of NAFLD corresponds to a reduction or a suppression of the abnormal accumulation of fat in the liver, and in the case of NASH, a suppression or a reduction of the inflammation, the fibrosis and/or the scarring of liver.

By "prevention" is meant, according to the invention, the prevention of the appearance of a disease, a disorder or one or more signs and/or symptoms. In particular, the prevention of NAFLD corresponds to the prevention of abnormal accumulation of fat in the liver, and in the case of NASH, the prevention of the inflammation, the fibrosis and/or the scarring of liver.

The prevention and treatment according to the invention apply to humans or animals.

In some embodiments, the compound according to the invention is:

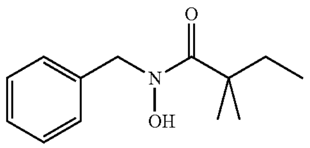

(N-Benzyl-N-hydroxy-2,2-dimethylbutanamide or "RIPA-56") or a pharmaceutically acceptable salt or hydrate thereof.

The compound "RIPA-56" is a selective and metabolically stable inhibitor of receptor-interacting protein kinase 1 (RIPK1) (Ren et al., J Med Chem 2017; 60(3): 972-986).

In some embodiments, the invention concerns the compound RIPA-56 or a pharmaceutically acceptable salt or hydrate thereof, for use in the prevention and/or treatment of NAFLD.

In some embodiments, the invention concerns the compound RIPA-56 or a pharmaceutically acceptable salt or hydrate thereof, for use in the prevention and/or treatment of hepatic steatosis.

In some embodiments, the invention concerns the compound RIPA-56 or a pharmaceutically acceptable salt or hydrate thereof, for use in the prevention and/or treatment of NASH.

In some embodiments, the compound according to the invention is a selective inhibitor of receptor-interacting protein kinase 1 (RIPK1). The selective inhibition of RIPK1 can be demonstrated via binding assays.

The compounds of the invention can be administered (either alone or in combination with other pharmaceuticals) in any conventional manner by any route where they are active. For example, administration can be, but is not limited to, by enteral route, in particular by oral or rectal administration, or by parenteral route, in particular by injection. The selection of the specific route of administration and the dose regimen is to be adjusted or titrated by the clinician according to methods known to the clinician to obtain the desired clinical response.

The compound or the composition according to the invention may be in any forms allowing its administration to the patient, for example a solution, a food, a beverage, a pill, a tablet, a syrup, a patch, a gum, a cream, a gel, a lotion, an ointment, a powder, a capsule, a vial, a suppository, etc . . . .

In preferred embodiments, the compound or the composition according to the invention is in a form allowing an oral administration.

The amount administered depends on the compound formulation, the severity of the condition being treated, the host, the route of administration, etc. It is generally empirically determined and can be adapted in routine trials.

Generally, the quantity of active compound in a unit dose of preparation may be varied or adjusted from about 1 to 1 000 mg, according to the particular application.

In an embodiment, the compound or the composition according to the invention is formulated into unit dose forms from 1 to 1 000 mg, in particular from 50 to 500 mg, more particularly from 100 to 300 mg of said compound.

In an embodiment, the compound or the composition according to the invention is formulated into unit dose forms of 1, 2, 3, 4, 5, 6, 7, 8, 9, 10, 20, 30, 40, 50, 60, 70, 80, 90, 100, 150, 200, 250, 300, 350, 400, 450, 500, 550, 600, 650, 700, 750, 800, 850, 900, 950 or 1 000 mg of said compound.

In an embodiment, the compound or the composition according to the invention is administered to a patient at a regimen of 1 to 1 000 mg per kg, in particular from 50 to 500 mg per kg, more particularly from 100 to 300 mg per kg.

The compound or the composition according to the invention can be administered one or more times per day. The regimen can be easily adjusted by the person skilled in the art or the clinician.

In an embodiment, the compound or the composition according to the invention is administered once daily, twice daily, three times daily or four times daily.

In an embodiment, the compound or the composition according to the invention is administered once weekly, twice weekly, three times weekly or four times weekly.

In an embodiment, the compound or the composition according to the invention is administered during a meal, preferably in the form of a food or a beverage.

In another aspect, the invention further relates to the use of the serum concentrations of RIPK1 and/or MLKL as biomarkers to detect NASH in a patient.

Indeed, the Inventors have surprisingly observed that the concentrations of the proteins RIPK1 and MLKL are increased, and correlate with transaminase activities, in the serum of patients with NASH.

This invention thus provides a useful tool to differentiate NASH from simple hepatic steatosis in a patient with NAFLD.

Another aspect thus relates to an in vitro or ex vivo method for diagnosing NASH in a patient comprising the steps of:

determining the concentration of the proteins RIPK1 and/or MLKL in a serum sample of said patient; and comparing the obtained value with a reference value;

wherein an increase of the concentration of the proteins RIPK1 and/or MLKL in the serum sample of a patient as compared to the reference value is indicative of NASH.

In an embodiment, said patient has already been diagnosed as suffering from NAFLD.

In an embodiment, the reference value corresponds to the concentration of RIPK1 and/or MLKL in a serum sample of a healthy individual.

In an embodiment, the reference value corresponds to the concentration of RIPK1 and/or MLKL in a serum sample of a patient with NAFLD.

In an embodiment, the reference value corresponds to the concentration of RIPK1 and/or MLKL in a serum sample of a patient with simple hepatic steatosis.

In an embodiment, the concentration of the proteins RIPK1 and/or MLKL is determined by an immunoassay, preferably by ELISA.

In an embodiment, an at least 2-fold increase of the concentration of the proteins RIPK1 and/or MLKL in the serum sample of a patient as compared to the reference value is indicative of NASH.

In an embodiment, an at least 3-fold increase of the concentration of the proteins RIPK1 and/or MLKL in the serum sample of a patient as compared to the reference value is indicative of NASH.

In an embodiment, an at least 4-fold increase of the concentration of the proteins RIPK1 and/or MLKL in the serum sample of a patient as compared to the reference value is indicative of NASH.

The following Examples are put forth so as to provide those of ordinary skill in the art with a complete disclosure and description of how to make and use the present invention, and are not intended to limit the scope of what the Inventors regard as their invention nor are they intended to represent that the experiments below are all or the only experiments performed. While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

FIGURES

FIG. 1. RIPA-56 prevents RIPK1-dependent cell death in L929 cells upon caspase inhibition and TNF stimulation. L929 cells were treated with RIPA-56 (20 μM), Nec-1 (20 μM) or vehicle for 2 h, prior to incubation with or without TNF (50 ng/mL), and analyzed for (A) morphology and (B) cell survival using MTT assay, after 20 h incubation with or without TNF; (C) Western blot analyses at different time points of incubation with TNF. Results are shown as mean±SEM; n.s., not significant; ****p<0.0001. Data are representative of three independent experiments.

Figure 2:
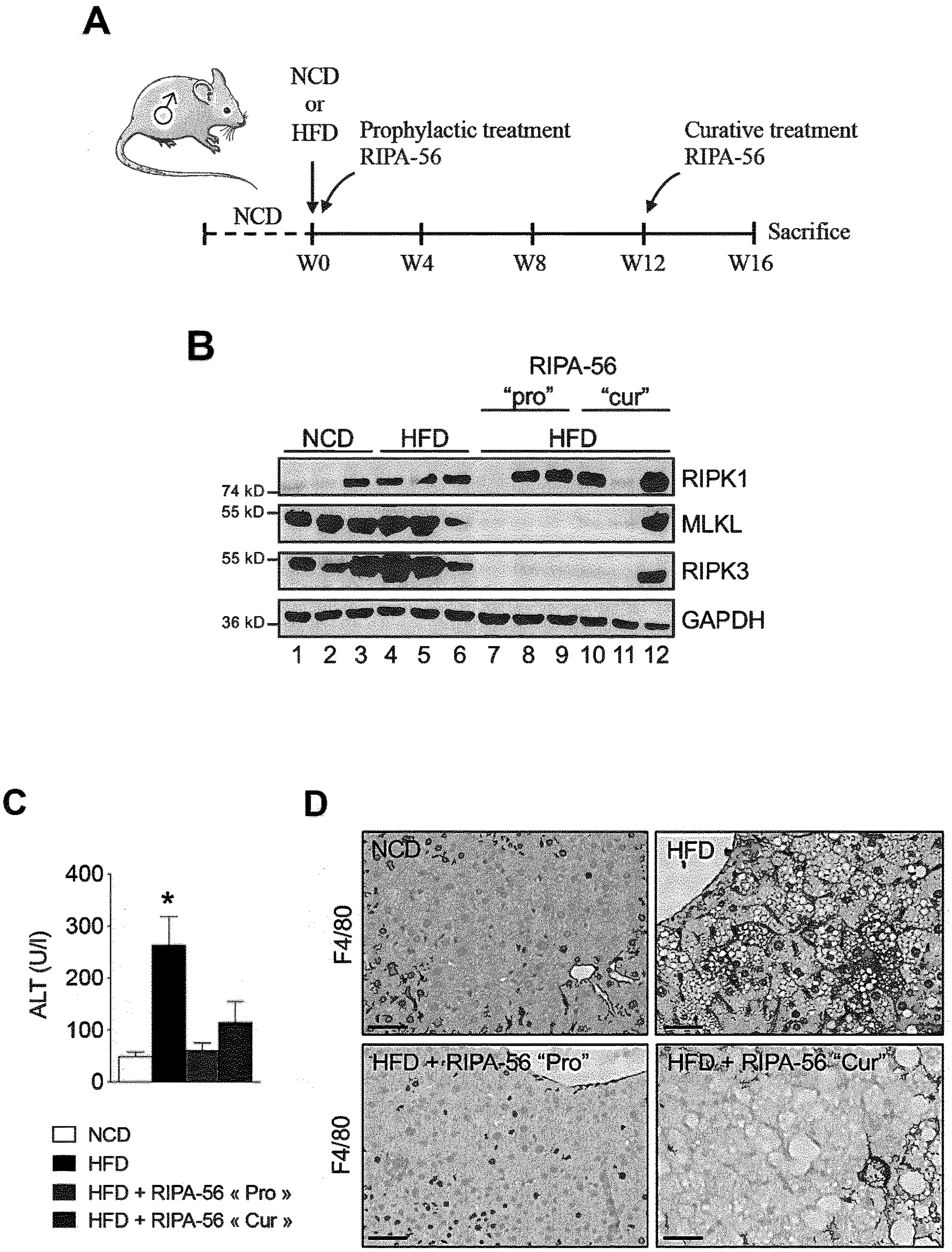
Figure 2:
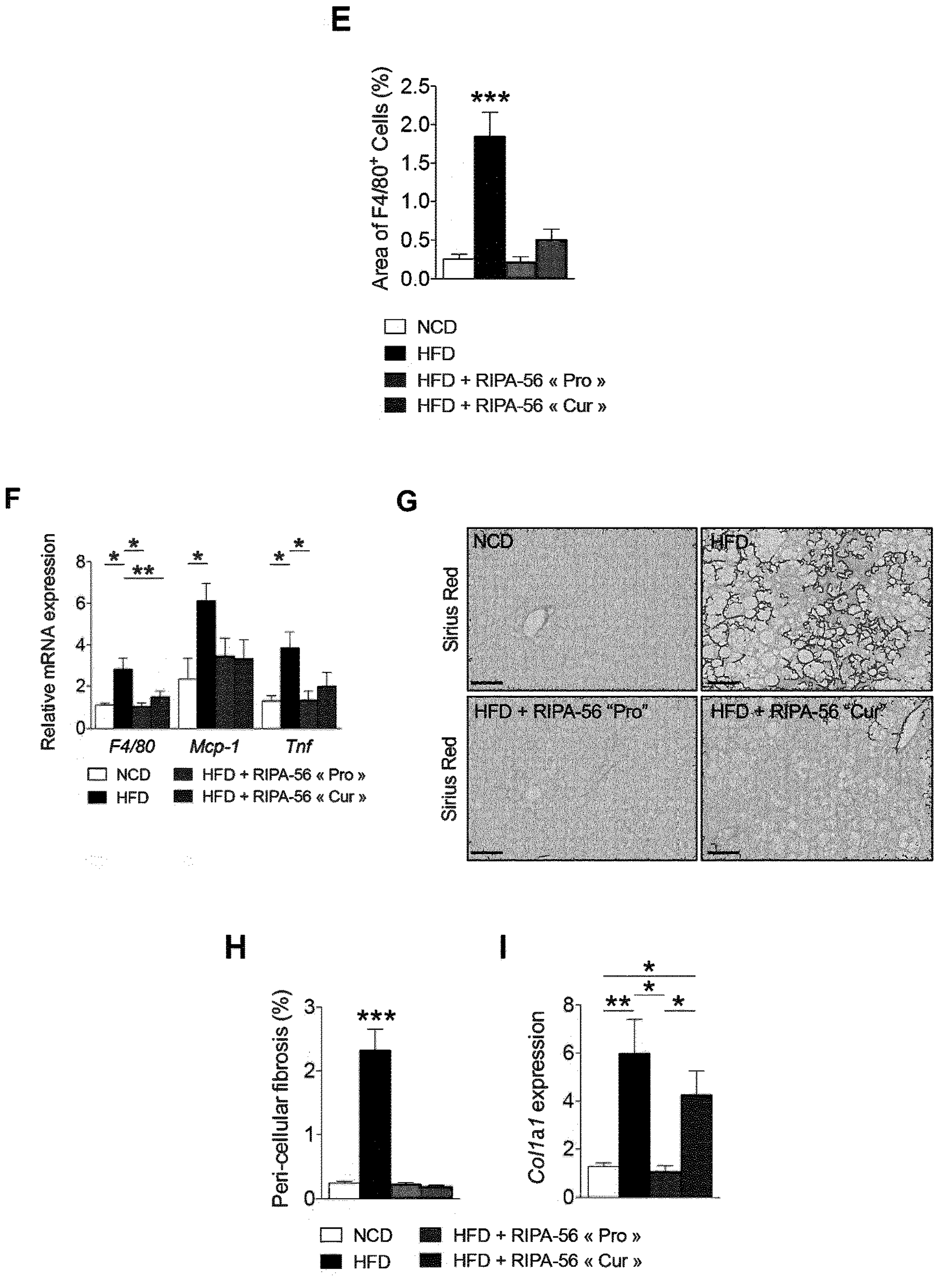

FIG. 2. RIPA-56 treatment improves liver inflammation and fibrosis in HFD-fed mice. Six-week-old male C57BL/6J mice (n=5 per group) were fed either with normal control diet (NCD) or high-fat diet (HFD) supplemented or not with RIPA-56, according to prophylactic ("Pro") or curative ("Cur") designs for 16 weeks, the time necessary for an inflammatory and fibrotic response to develop. Differences between mice were determined by analysis of variance (ANOVA) with Bonferroni's multiple comparison. (A) Schematic representation of the experimental design; (B) Immunoblot analyses of whole liver protein extracts from mice fed NCD (1 to 3), HFD (4 to 6), HFD with RIPA-56 "Pro" (7 to 9), or HFD with RIPA-56 "Cur" (10 to 12) using antibodies against RIPK1, MLKL, RIPK3 and GAPDH as loading control; (C) Serum analysis of ALT; (D) Immunohistochemical analysis of F4/80 on representative liver tissue sections from mice of each group; (E) Quantitative analysis of F4/80$^+$ foci using ImageJ software, 10 pictures per mouse were quantified; (F) F4/80, Mcp-1 and Tnf mRNA levels were assessed by RT-qPCR. (G) Representative Sirius Red staining of liver tissue section from mice of each group; (H) Quantification of light polarized Sirius Red pictures, 10 pictures per mouse were analyzed; (I) Collal mRNA levels were assessed by RT-qPCR. All data are expressed as mean±SEM; *p<0.05; p<0.01; *p<0.001. Scale bars indicate 50 μm.

Figure 3:
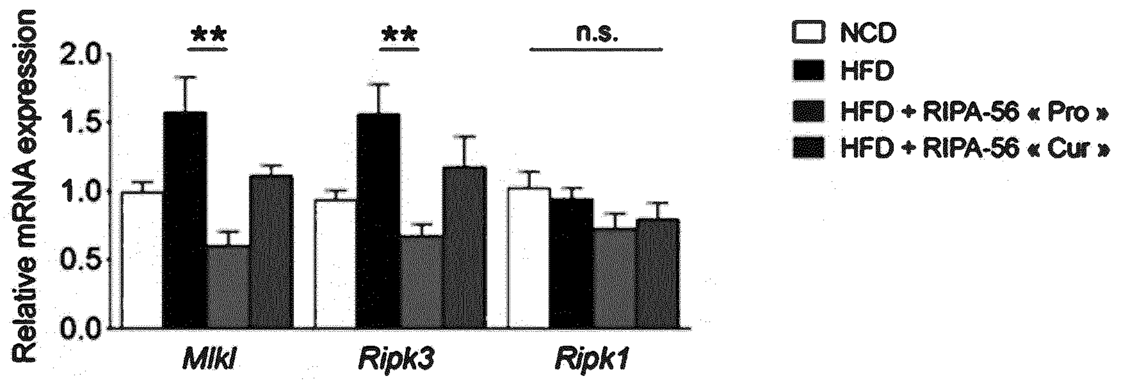

FIG. 3. mRNA expression levels of MLKL, RIPK3 and RIPK1 in the liver of prophylactically- and curatively-treated mice compared with control mice under HFD. mRNA levels of Mlkl, Ripk3 and Ripk1 were assessed by RT-qPCR, and shown relative to NCD-fed mice. Differences between groups (n=5) were determined by one-way ANOVA with Bonferroni's multiple comparison. Results are shown as mean±SEM; **p<0.01; n.s. not significant.

Figure 4:
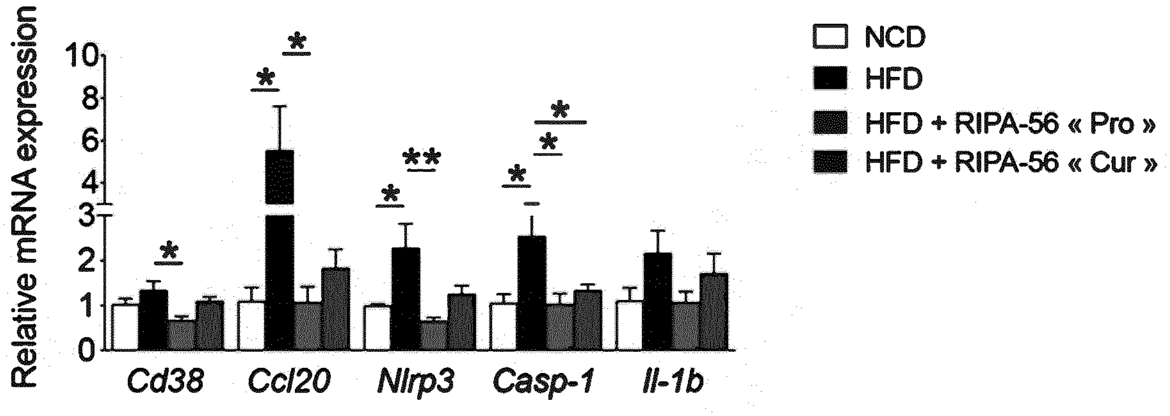

FIG. 4. mRNA expression of inflammatory markers in the liver of prophylactically- and curatively-treated mice compared with control mice under HFD. mRNA levels of Cd38, Ccl20, Nlrp3, Caspase-1, Il-1b were assessed by RT-qPCR, and shown related to NCD-fed mice. Differences between groups (n=5) were determined by one-way ANOVA with Bonferroni's multiple comparison. Results are shown as mean±SEM; **p<0.01; n.s. not significant.

Figure 5:
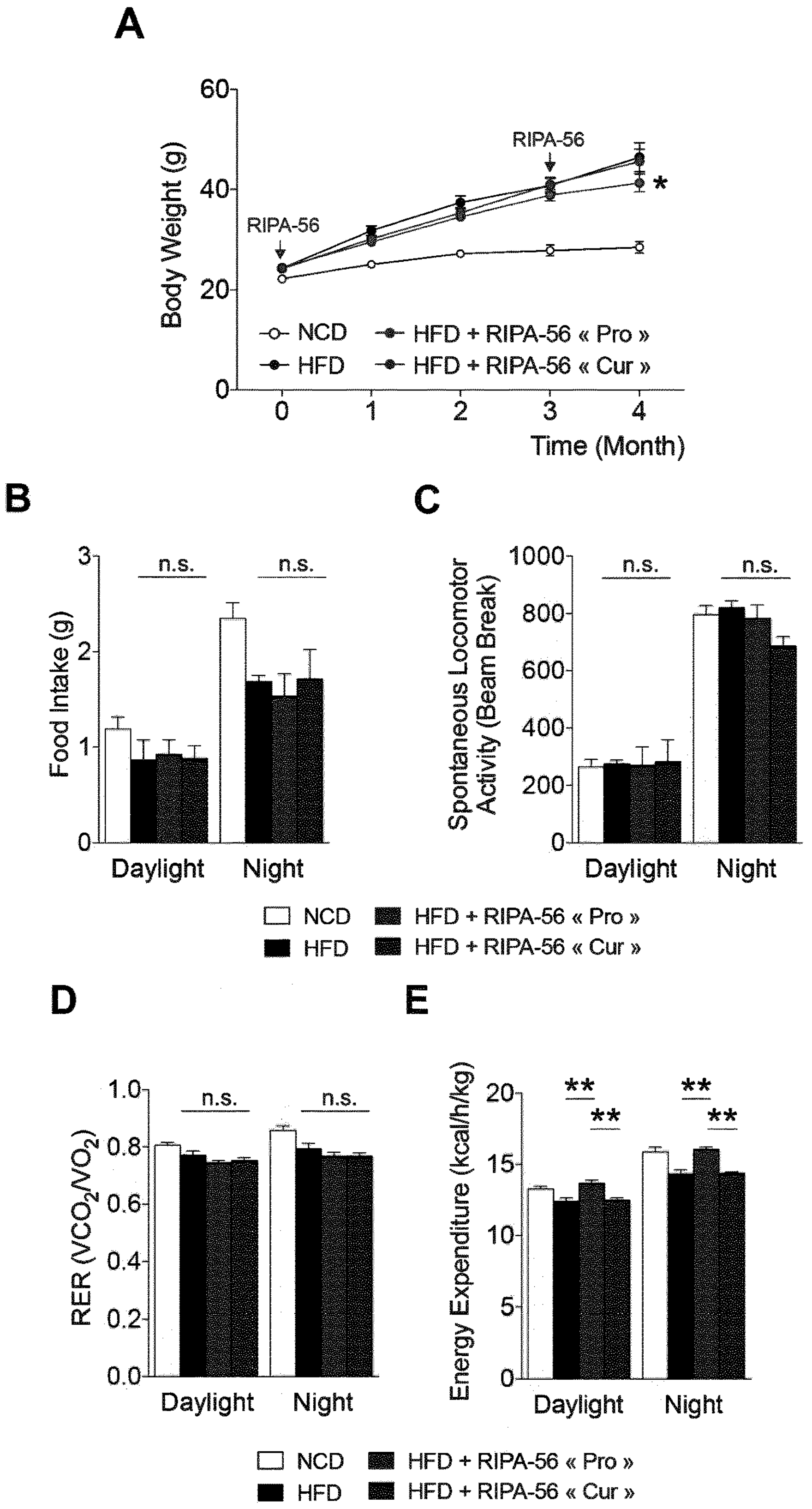
Figure 5:
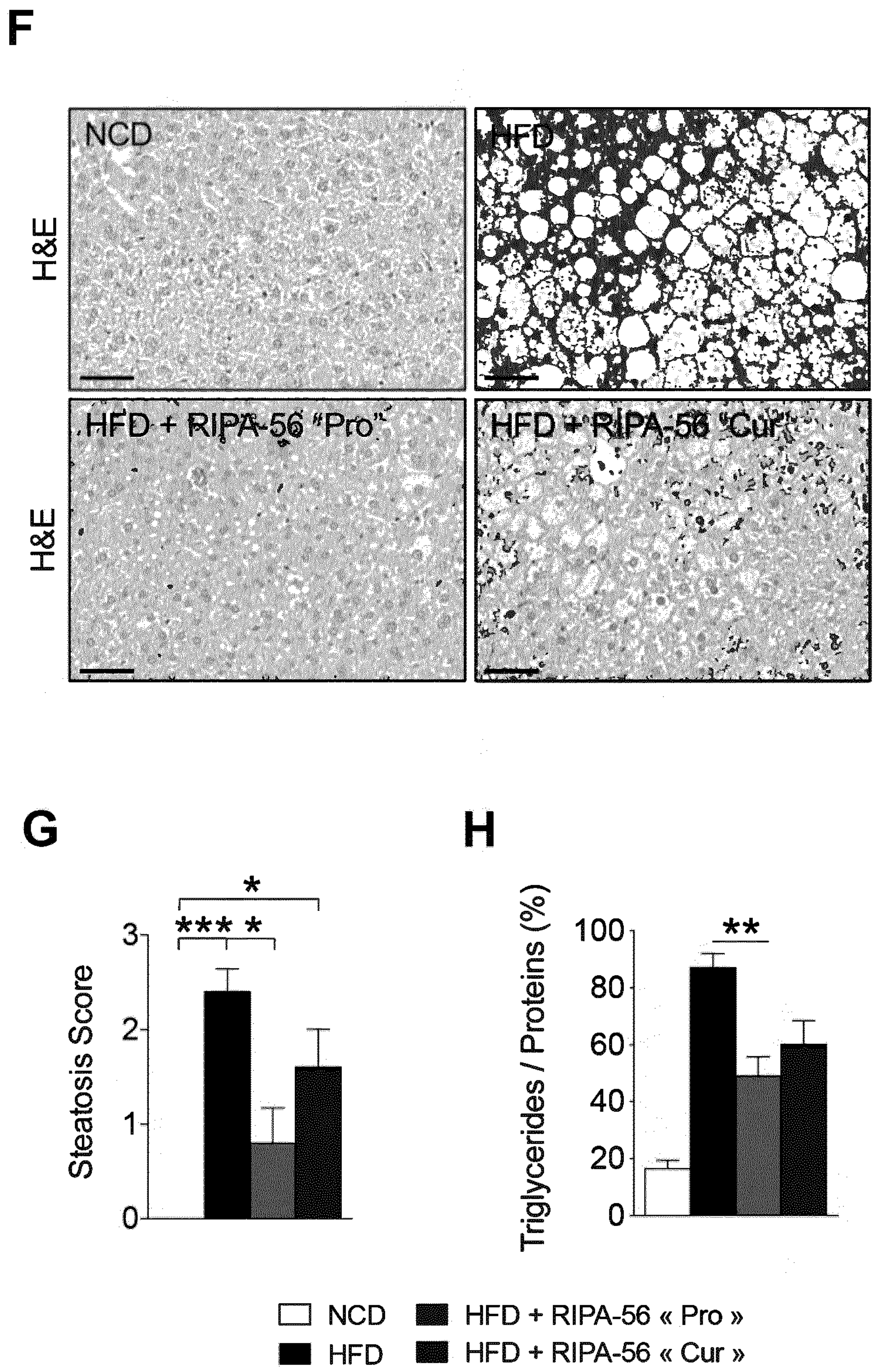

FIG. 5. RIPA-56 treatment improves HFD-induced obesity and steatosis in mice. Six-week-old male C57BL/6J mice (n=5 per group) were fed either NCD or HFD supplemented or not with RIPA-56 for 16 weeks, as depicted in FIG. 2A, to analyze the metabolic status of the mice. (A) Body weight gain in mice of the 4 groups. No significant change in (B) food intake, (C) spontaneous locomotor activity, or (D) respiratory exchange ratio (RER) in mice Of the 4 groups; (E) Whole energy expenditure was evaluated during daylight and night in mice of the 4 groups; (F) Representative H&E staining of liver tissue sections from mice of the 4 groups. Scale bars, 50 μm; (G) Steatosis score of liver tissue sections was evaluated blinded; (H) Intrahepatic triglyceride contents were measured in two liver samples per mouse. Results are shown as mean±SEM; *p<0.05; p<0.01; *p<0.001.

Figure 6:
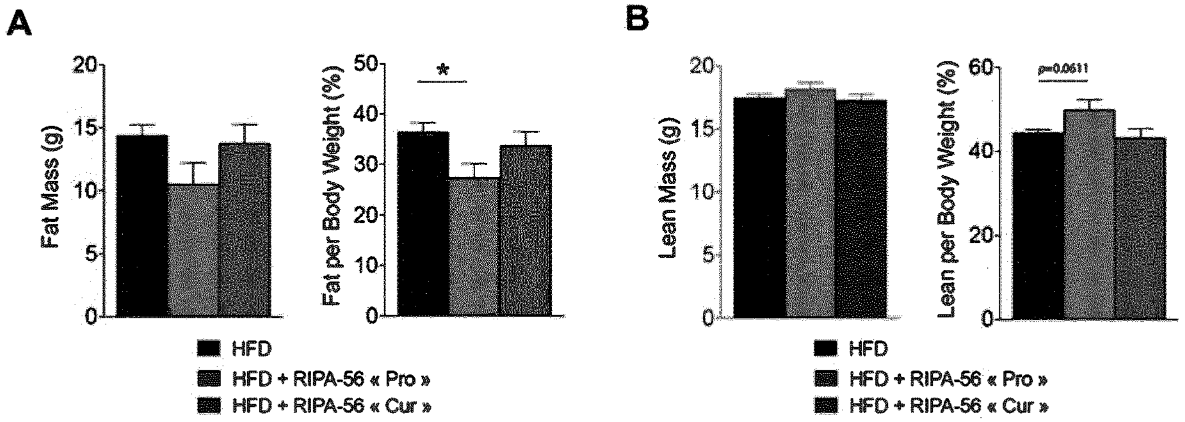

FIG. 6. Fat and lean mass in prophylactically- and curatively-treated mice compared with control mice under HFD. (A) Body fat mass and relative body fat content, and (B) lean mass and relative lean content were evaluated in HFD-fed mice using MRI analysis. All results are shown as mean±SEM; n=5 per group; *p<0.05. Differences between groups were determined by one-way ANOVA with Bonferroni's multiple comparison.

Figure 7:
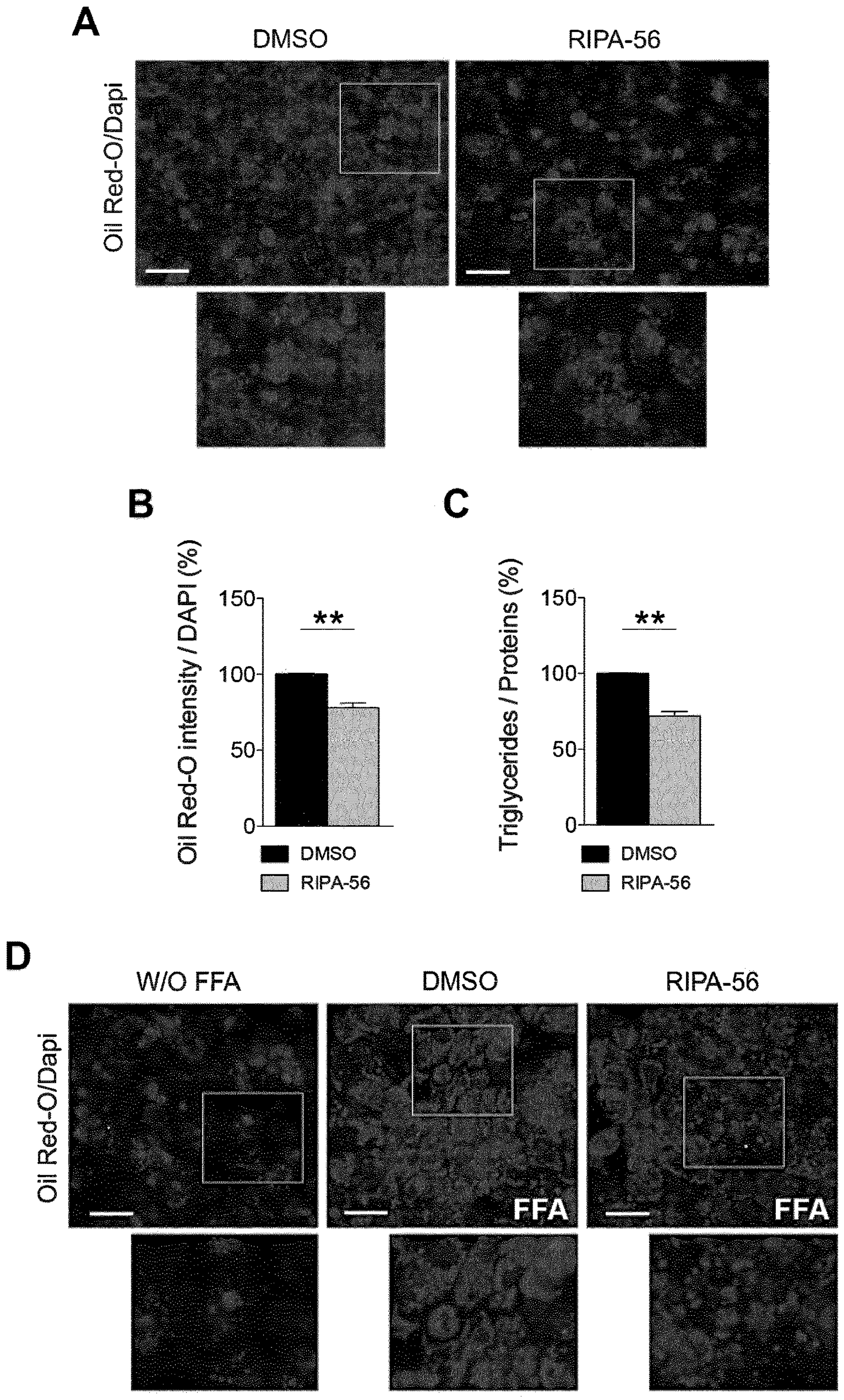
Figure 7:
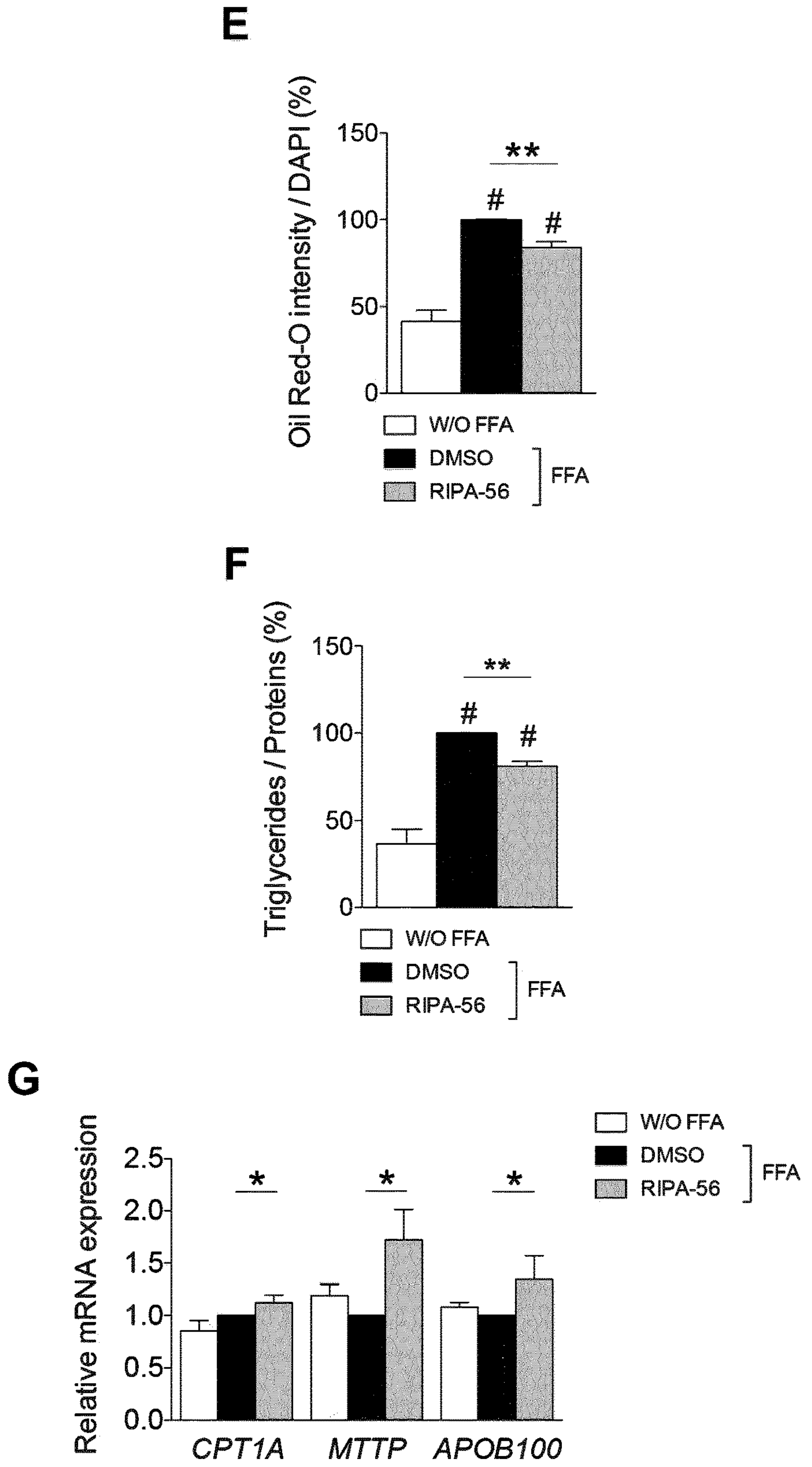

FIG. 7. RIPA-56 treatment induces fat depletion in primary human hepatocytes. Primary human hepatocytes were isolated from steatotic human livers of patients with NAFLD (n=5) (A-C) or from non-steatotic human livers and incubated with free fatty acids to induce steatosis or without (W/O) (n=5) (D-G), and treated with RIPA-56 (20 μM) or DMSO (vehicle) for 24 h. (A, D) Representative Oil Red-O and DAPI images; (B, E) Quantification of Oil Red-O staining normalized for the number of DAPI-stained nuclei; (C, F) Quantification of intracellular triglycerides normalized to protein content; (G) mRNA levels of CPT1A, MTTP and APOB100 were assessed by RT-qPCR, and shown relative to DMSO-treated hepatocytes. Results are shown as mean±SEM; n.s., not significant; *p<0.05; **p<0.01; scale bars, 100 μm. These findings are representative of five independent cell preparations.

Figure 8:
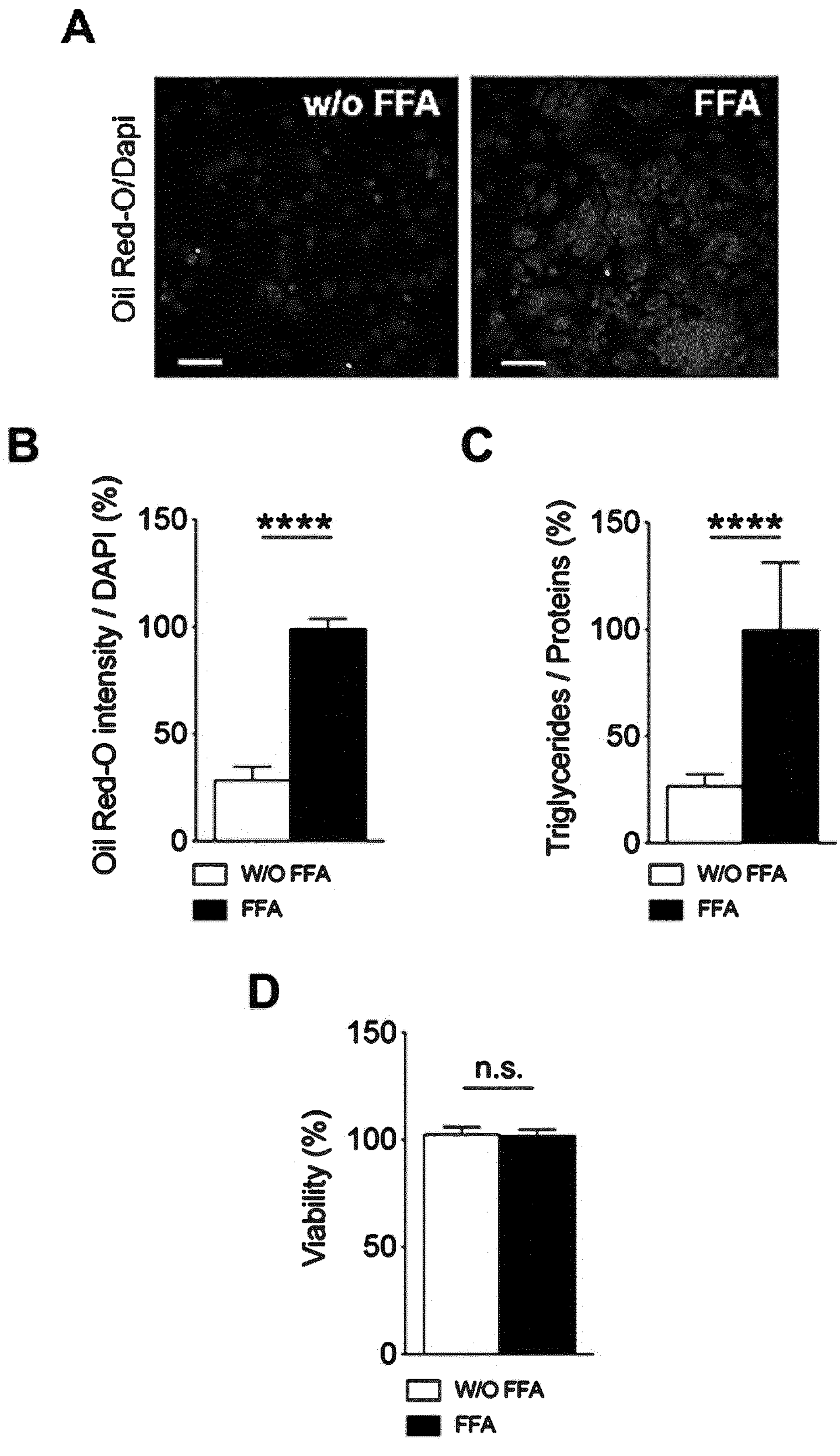

FIG. 8. Steatosis induction in primary human hepatocytes using free fatty acids for 48 h. (A) Representative images of PHH incubated with or without FFA (oleic acid and palmitic acid); Quantification of Oil Red-O staining (B) and intracellular triglyceride content (C); (D) Cell viability analysis was performed using an MTT assay. Results are shown as mean±SEM; n.s., not significant; ****p<0.0001. Data are representative of five independent experiments. Differences between w/o FFA and FFA were determined using Student's t-test.

Figure 9:
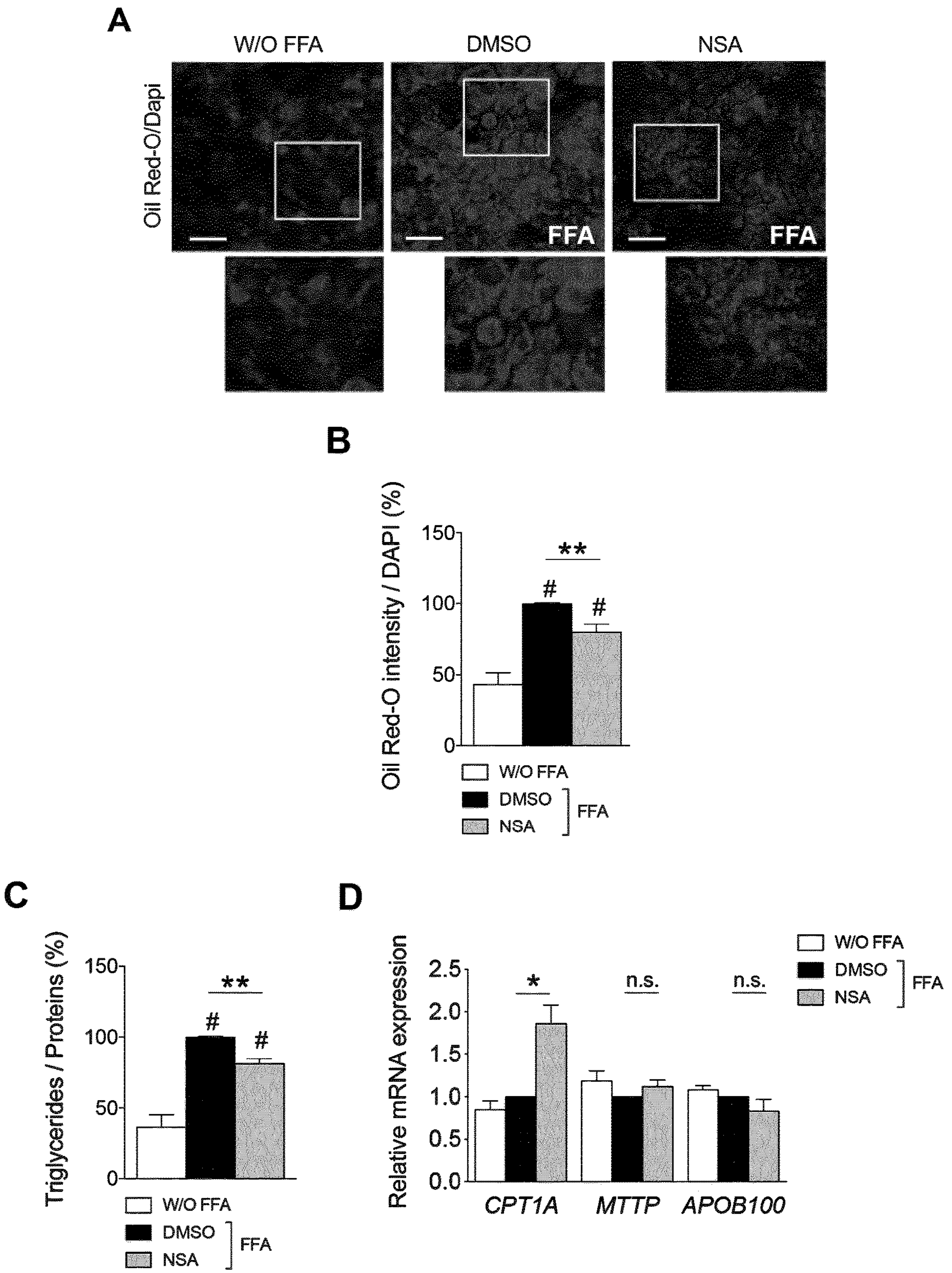
Figure 9:
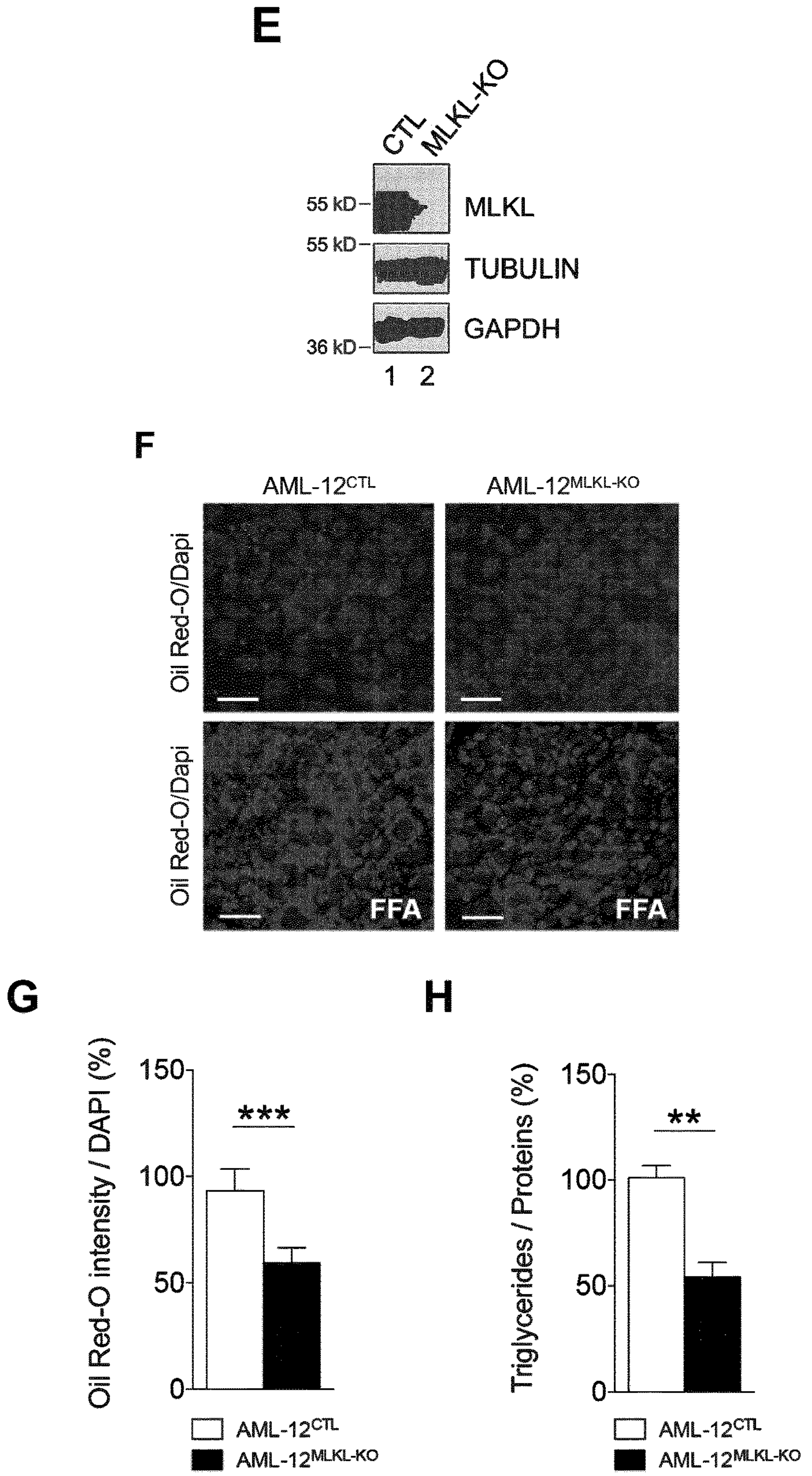

FIG. 9. MLKL controls intrahepatic triglyceride content in hepatocytes. (A-D) Primary human hepatocytes were isolated from non-steatotic human livers and incubated with free fatty acids to induce steatosis, or without (W/O), and treated with necrosulfonamide (NSA) (20 μM) or DMSO (vehicle) for 24 h. (A) Representative Oil Red-O and DAPI images; (B) Quantification of Oil Red-O staining normalized for the number of DAPI-stained nuclei; (C) Quantification of intracellular triglycerides normalized to protein content. (D) mRNA levels of CPT1A, MTTP and APOB100 were assessed by RT-qPCR and shown relative to DMSO-treated hepatocytes; (E-H) AML-12 cells were knocked-out (KO) for MLKL and compared with control (CTL) cells, which underwent a similar CRISPR-Cas9 selection as KO cells; (E) Whole-cell lysates were extracted from CTL and MLKL-KO AML-12 cells and analyzed by Western blot using antibodies against MLKL, Tubulin and GAPDH; (F) Representative Oil Red-O and DAPI images; (G) Oil Red-O staining and (H) triglycerides quantification in fat-loaded cell lines. Results are shown as mean±SEM; n.s., not significant; *p<0.05; p<0.01; *p<0.001; scale bars, 100 μm. These experiments are representative of five independent cell preparations.

Figure 10:
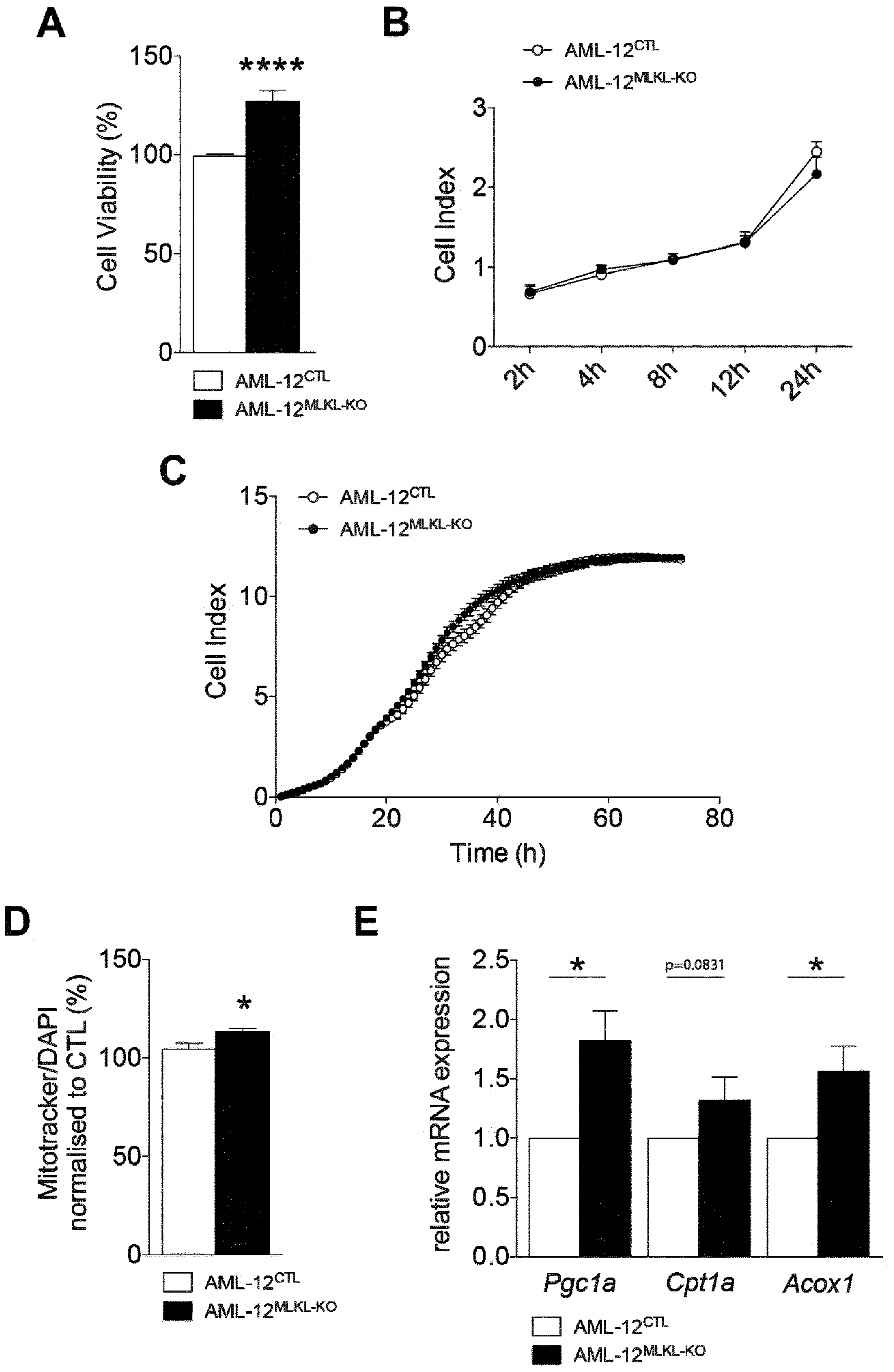
Figure 10:
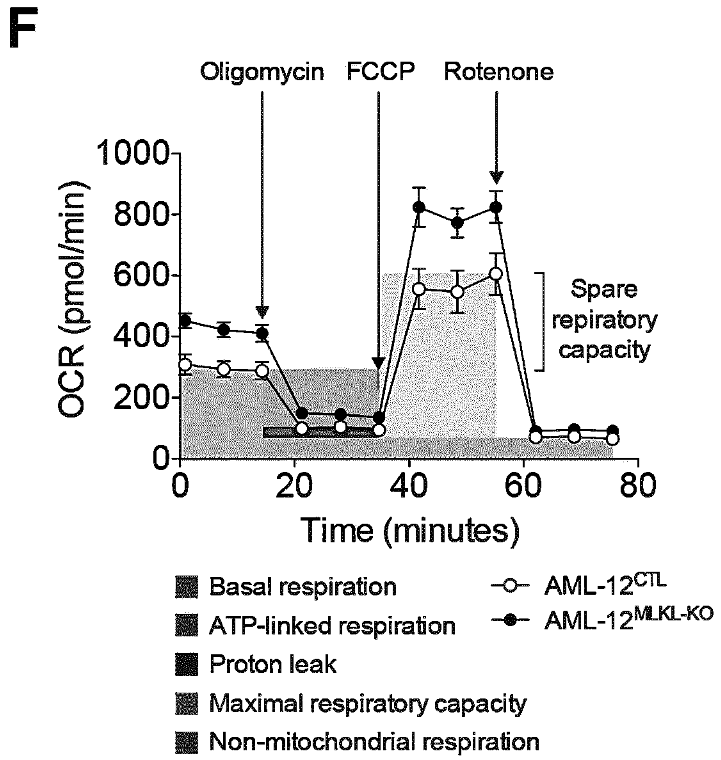
Figure 10:
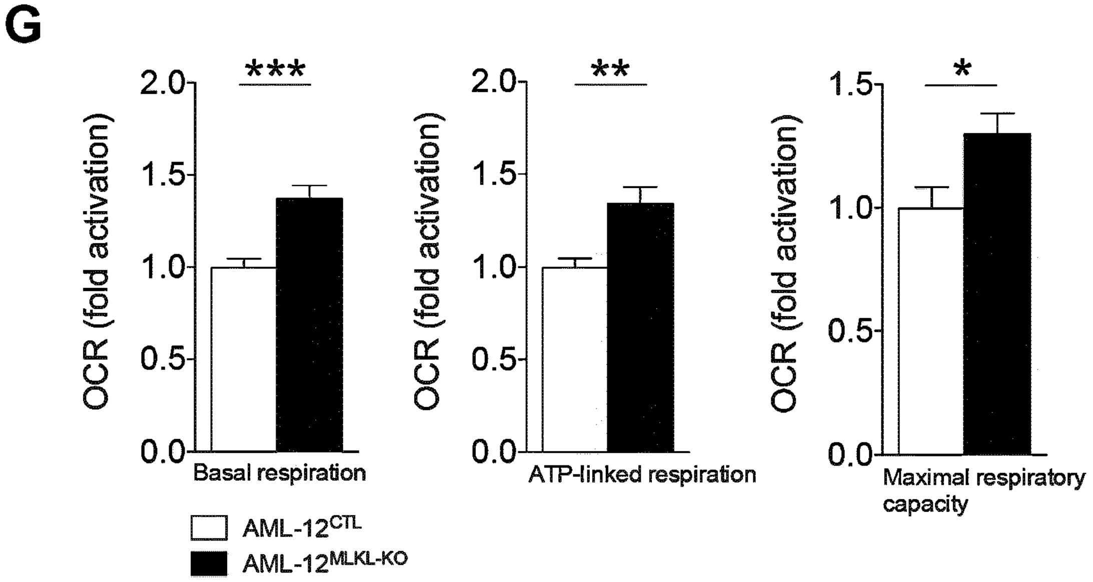

FIG. 10. MLKL regulates mitochondrial respiration in murine hepatocytes. AML-12 cells were knocked-out (KO) for MLKL and compared with control (CTL) cells, which underwent a similar CRISPR-Cas9 selection as KO cells. (A) Cell viability was analyzed using the MTT assay; Cell proliferation was analyzed using (B) BrdU incorporation and (C) real-time cell analysis (xCELLigence Cim-Plate 96). Each cell line was seeded in six replicate wells; (D) The mitochondrial mass was evaluated using a MitoTracker Red-Probe in triplicate; (E) mRNA levels of Pgc1a, Cpt1a and Acox1 were assessed by RT-qPCR in triplicate; (F) The respiratory flux profiles of cells were determined using a Seahorse Extracellular Flux Analyzer with twelve consecutive measurements of oxygen consumption rate (OCR). Each cell line was seeded in eight replicate wells; (G) Basal mitochondrial OCR, ATP-linked OCR, maximum OCR are represented as fold activation. Results are shown as mean±SEM of 8 replicates; n.s.: not significant; *p<0.05; p<0.01; *p<0.001; ****p<0.0001. Differences between CTL and KO cells were determined using Student's t-test. All experiments are representative of three independent cell preparations.

Figure 11:
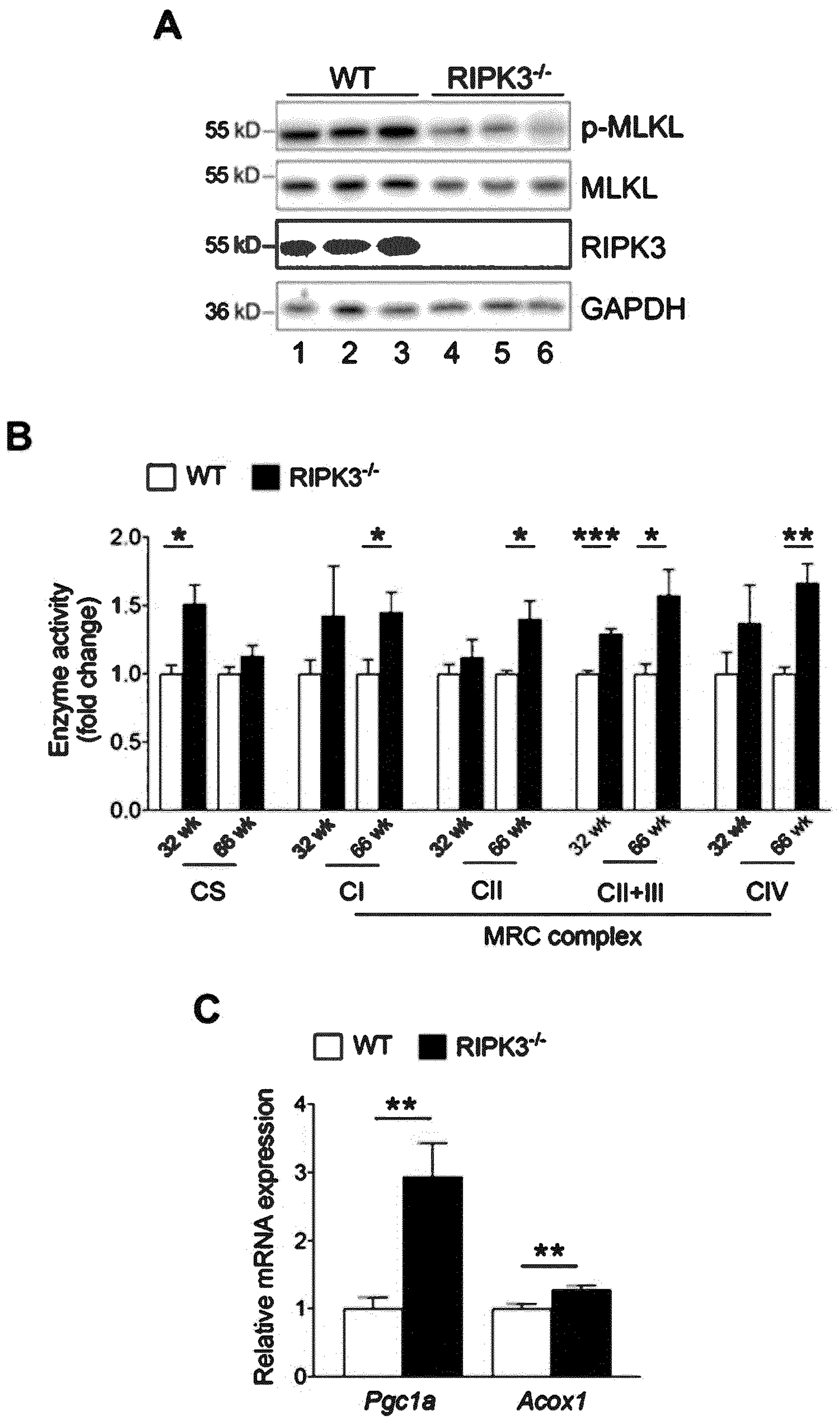

FIG. 11. Mitochondrial bioenergetics are enhanced in RIPK3-deficient mice fed a CDAA. (A) Immunoblot analyses of whole liver protein extracts from WT mice (1 to 3) and RIPK3$^{-/-}$ mice (4 to 6) fed a CDAA for 32 weeks using antibodies against p-MLKL, MLKL, RIPK3 and GAPDH as loading control; (B) Citrate synthase (CS) and mitochondrial respiratory chains (MRC) activities in WT vs. R1PK3$^{-/-}$ mice (n=7) fed a CDAA for 32 weeks or 66 weeks; (C) Pgc1a and Acox1 mRNA levels were assessed by RT-qPCR, and shown related to WT mice (n=7). All data are expressed as mean±SEM; *p<0.05; p<0.01; *p<0.001. Differences between WT and RIPK3$^{-/-}$ mice were determined using Student's t-test.

Figure 12:
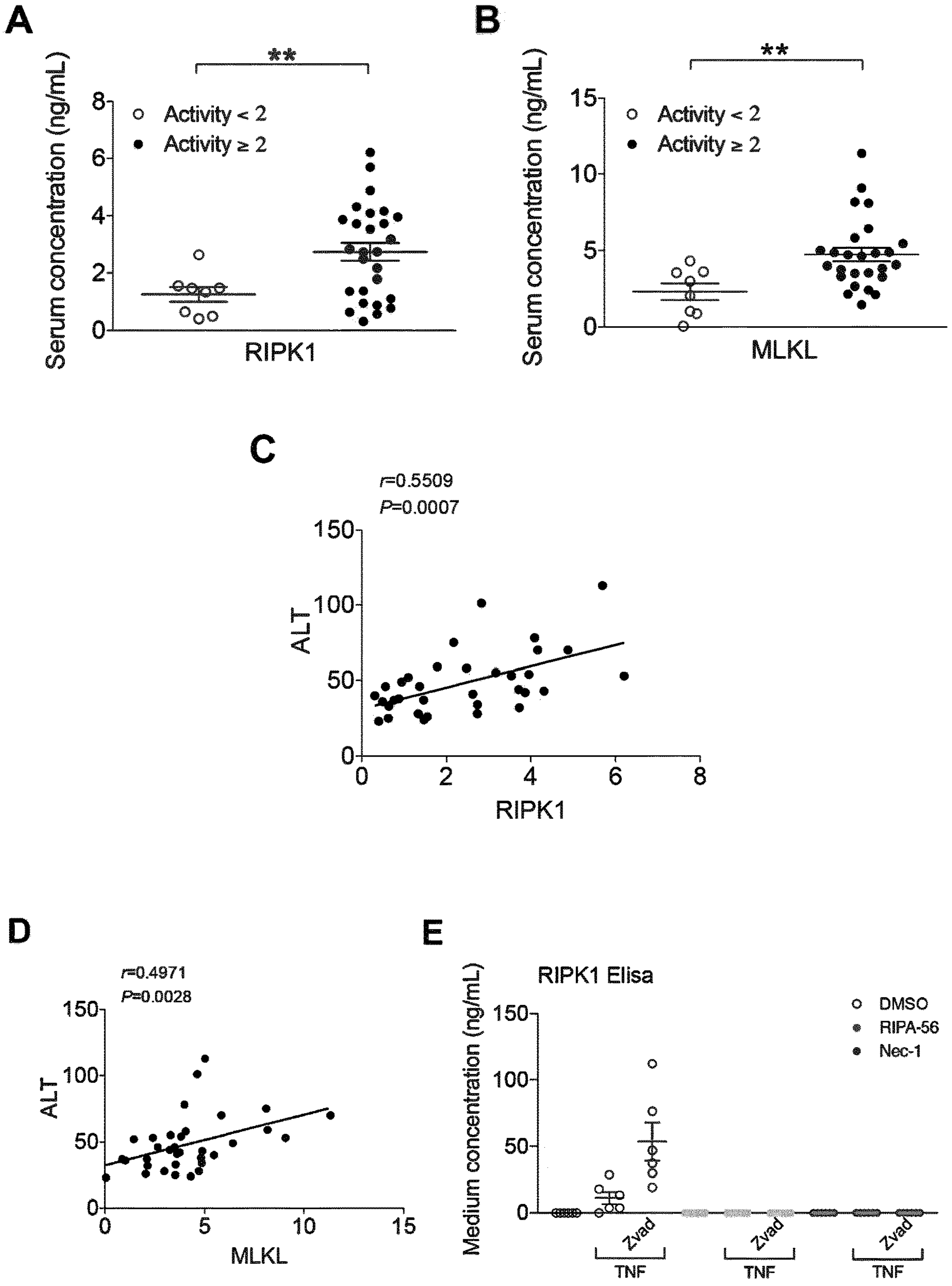

FIG. 12. RIPK1 and MLKL are released extracellularly during necroptosis. (A-B) ELISA analysis of RIPK1 and MLKL protein levels in the serum of subjects with NAFLD and a histological activity score <2 (n=8) or ≥2 (n=27); **p<0.01; (C-D) Correlation plot analysis between RIPK1 or MLKL and ALT levels in all subjects, $r^2$ values were calculated with Pearson's correlations; (E) ELISA analysis of RIPK1 in the supernatant cleared from debris of L929 cells treated with the pan-caspase inhibitor Zvad (20 μM), RIPA-56 (20 μM), necrostatin-1 (Nec-1, 20 μM) or vehicle (DMSO) for 2 h, prior to incubation with or without TNFα (25 ng/mL) for 6 h. Results are shown as mean±SEM of six replicates.

Figure 13:
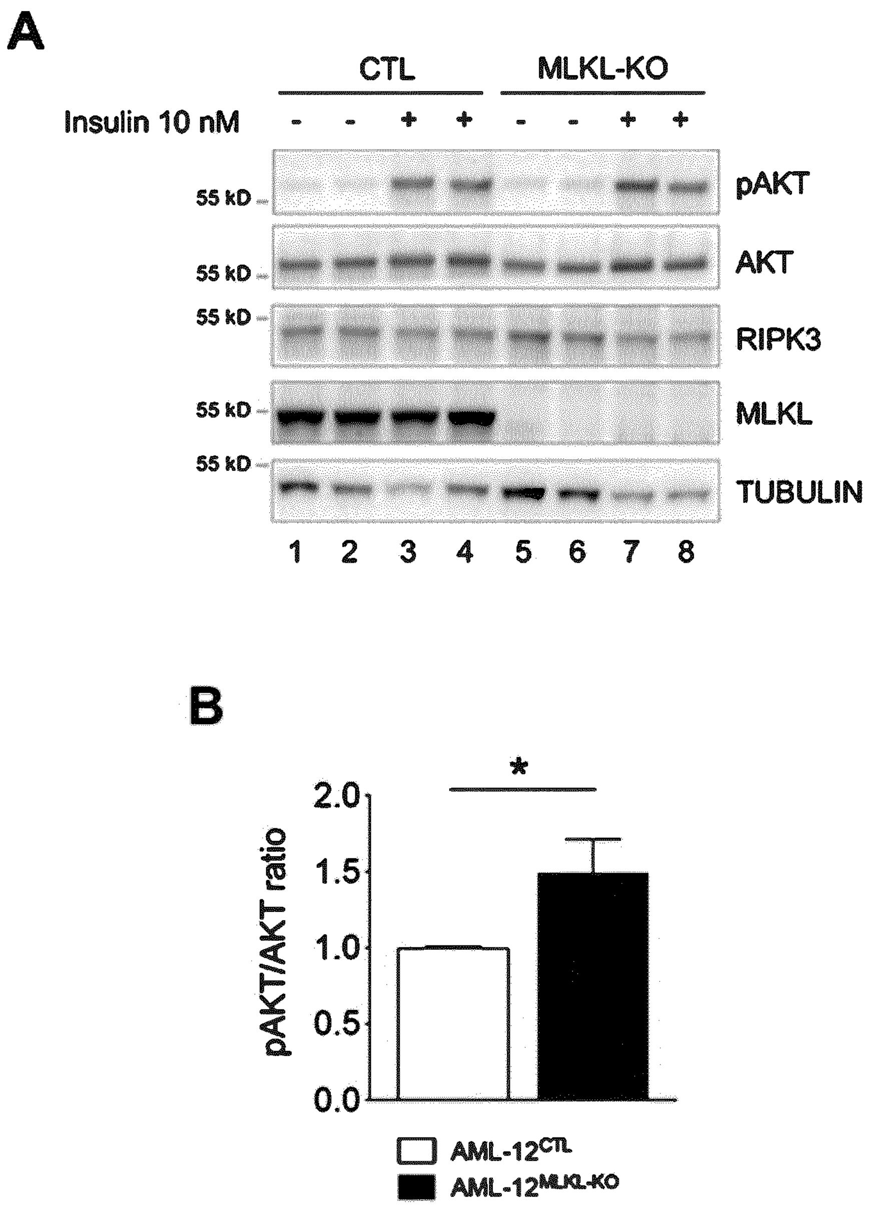

FIG. 13. MLKL regulates insulin signaling. (A) Immunoblot analyses in AML-12$^{CTL}$ and AML-12$^{MLKL\text{-}KO}$ cells stimulated with insulin (10 nM) for 15 minutes. (B) Semi-quantitative analysis of immunoblots insulin-stimulated cells (n=3). Results are expressed as mean±SEM; *p<0.05. Differences between AML-12$^{CTL}$ and AML-12$^{MLKL\text{-}KO}$ cells were determined using Student's t-test. Data are representative of three independent experiments.

EXAMPLES

Materials & Methods

RIPA-56 Feeding Experiment

Six-week-old male C57BL/6J mice (Charles River Laboratories, Ecully, France) were fed a high-fat diet (HFD—45 kcal % fat) or a normal chow diet (NCD) (Ssniff spezialdiäten GmbH, Soest, Germany) for 16 weeks (the time necessary for an inflammatory and fibrotic response to develop). The effects of a highly potent and highly specific RIPK1 kinase inhibitor (referred as to RIPA-56) were evaluated by incorporating it into HFD at 300 mg/kg dose as initially described.

Patients

Serum samples were obtained from 35 subjects with NAFLD (Table 1). The study population was divided in two groups based on the histological score of activity, i.e., the sum of hepatocyte ballooning and lobular inflammation. The first group included subjects with a score <2, and the second, subjects with a score ≥2. Human samples were processed and stored by the Biological Resource Center, Bio-ICAN, Institute of Cardiometabolism and Nutrition (IHU-ICAN, ANR-10-IAHU-05), Paris, France. All subjects gave written informed consent before taking part in the study.

Isolation and Culture of Primary Human Hepatocyte (PHH)

Ethical approval for the isolation of human hepatocytes was granted by the Persons Protection Committee (CPP Ile de France III) and by the French Ministry of Health (N°: COL 2929 and COL 2930). Liver tissue was obtained from subjects undergoing partial hepatectomy for the treatment of colorectal cancer metastases. Cell isolation was performed on Human HepCell platform (IHU-ICAN, Paris, France), as previously described.

Real-Time Quantitative PCR (RT-qPCR)

Total RNA was extracted using RNeasy columns (Qiagen, Courtaboeuf, France). The mRNA levels of selected genes were calculated after normalization to Hprt, Hmbs or GAPDH by using the ΔΔCt method.

Statistical Analysis

Sample size was calculated using size power analysis methods (GraphPad StatMate) for a priori determination based on the standard deviations of previous experiments. The minimal sample size for each group was calculated as five animals. Animals with same sex and same age were employed to minimize physiological variability. Student t test or analysis of variance (ANOVA) were used to compare two groups and three or more groups, respectively. GraphPad Prism software (version 6.0) was used to calculate statistical significance. Statistical tests were used as described in the Figure legends and statistical significance was indicated as follows: *p<0.05; p<0.01; *p<0.001; ****p<0.0001; n.s., not significant. All data are expressed as mean±SEM.

RIPA-56 Feeding Experiment

RIPA-56 (MedChemExpress, Stockholm, Sweden) was incorporated in diet by Ssniff spezialdiäten GmbH (Soest, Germany) according to a standardized protocol. Ssniff company is an approved manufacturer of laboratory animal diets and has the license to produce medicated feed for laboratory animals in accordance with Directive 2001/82/EC. Before the end of the feeding period, mice were single housed for one week in metabolic cages to measure food intake, respiratory exchange ratio (RER), energy expenditure and spontaneous locomotor activity using a LabMaster indirect calorimetry system (TSE Systems GmbH, Bad Homburg, Germany). Mice were sacrificed under anesthesia and blood was collected via intracardiac puncture procedure. Tissue samples were either directly snap-freezed in liquid nitrogen for molecular analysis or fixed in 4% PFA and embedded in paraffin for histological analysis. All experiments were conducted in the SPF animal facility of CRSA (Agreement No. C-75-12-01), according to the European Communities Council Directive (2010/63/UE) for the care and use of animals for experimental procedures and complied with the regulations of the French Ethics Committee of Animal Experiments «Charles Darwin» registered at the «Comité National de Réflexion Ethique sur l'Experimentation Animale» (Ile-de-France, Paris, n° 5). All procedures were approved by this committee (n° B751201).

RIPK3 KO Mice Feeding Experiment

Seven-to-eight weeks old male C57BL/6 wild-type and RIPK3-KO mice were fed a choline-deficient, amino-acid-defined diet (CDAA; Envigo, Madison, USA) for 32 weeks (to induce NASH) or 66 weeks. Seven animals were included in each experimental group. At the indicated time-points, animals were fasted for 4 hours and sacrificed by $CO_2$ overdose followed by exsanguination. The liver was removed and one lobe was collected, rinsed in normal saline and immediately flash-frozen in liquid nitrogen for further molecular analyses. All animal experiments were carried out with the permission of the local animal ethical committee in accordance with the EU Directive (2010/63/EU), Portuguese law (DL 113/2013) and all relevant legislations. The experimental protocol was approved by Direcção Geral de Alimentação e Veterinária, Portugal. Animals received humane care in a temperature-controlled environment with a 12-h light—dark cycle, complying with the Institute's guidelines and as outlined in the 'Guide for the Care and Use of Laboratory Animals' prepared by the National Academy of Sciences and published by the National Institutes of Health (NIH publication 86-23 revised 1985).

Cell Lines & Reagents

L929 cells (LGC Standards, Molsheim, France), were cultured in Dulbecco's modified Eagle's medium (DMEM) (ThermoFisher, Massachusetts, USA) supplemented with 10% fetal bovine serum (Eurobio, Courtaboeuf, France), penicillin (100 IU/ml), streptomycin (0.1 mg/ml), and L-glutamine (0.03%) (ThermoFisher). L929 cells were treated by Zvad (#sc-3067, 20 μM; Santa Cruz Biotechnologies, Dallas, USA), Nec-1 (#sc-200142, 20 μM); RIPA-56 (#HY-101032, 20 □M; MedChemExpress, Sollentuna, Sweden) and TNFα (#315-01A, 20 ng/ml; Peprotech, Neuilly-sur-Seine, France). AML-12 (alpha mouse liver-12) hepatocytes (LGC Standards) were cultured in DMEM/F12 Medium (ThermoFisher) supplemented with 10% fetal bovine serum (Eurobio), 10 μg/ml insulin, 5.5 μg/ml transferrin, 5 ng/ml selenium and 40 ng/ml dexamethasone (Sigma, Missouri, USA). AML-12 hepatocytes were stimulated with insulin (#I0516, 10 nM; Sigma) for 15 minutes.

CRISPR/Cas9-Mediated Deletion of Mlkl pSpCas9(BB)-2A-GFP (PX458) was used to transfect AML-12 cells with Cas9 along with the targeting guide RNAs (gRNAs). Guide RNAs were designed and checked for efficiency and specificity. Subsequently, they were cloned in the plasmid and transfected into cells using TurboFect (ThermoFisher, Massachusetts, USA) transfection reagent accordingly to the manufacturer's instructions. After 48 h of transfection, cells were sorted by flow cytometry (Cell Sorting Core Facility, Centre de Recherche Saint-Antoine) and cells with the highest GFP positivity were finally transferred as single cells into 96-well plates and propagated.

Isolation and Culture of Primary Human Hepatocyte (PHH)

The liver fragment was initially perfused with a pre-warmed (37° C.) calcium-free buffer supplemented with 5 mmol/L ethylene glycol tetra-acetic acid (Sigma) followed by perfusion with a prewarmed (37° C.) buffer containing 6 mmol/L calcium ($CaCl_2$) and collagenase 0.05% (5 mg/mL) (Sigma). The liver fragment was then gently shaken to disperse liver cells in Hepatocyte Wash Medium (Life Technologies, Villebon-sur-Yvette, France). The resulting cell suspension was filtered through a gauze-lined funnel. Cells were then centrifuged at low speed. The supernatant, containing damaged or dead hepatocytes, non-parenchymal cells and debris were removed and pelleted hepatocytes were re-suspended in Hepatocyte Wash Medium. The count of viable cells was determined using trypan blue exclusion. Freshly isolated normal (steatosis <5%) or steatotic (>10%) hepatocytes were resuspended in Williams medium E (Life technologies) containing 10% fetal calf serum (Eurobio), penicillin (200 U/mL)-streptomycin (200 μg/mL), Fungizone (2.5 μg/mL) and insulin (0.1 U/mL) (Life Technologies). The cells were seeded in 12-, 24- and 96-well plates pre-coated with type I collagen at a density of $0.78\times10^6$, $0.4\times10^6$ and $0.5\times10^5$ viable cells/well, respectively, and incubated overnight at 37° C. in a 5% $CO_2$ atmosphere. The medium was replaced with fresh complete hepatocyte medium supplemented with 1 μmol/L hydrocortisone hemisuccinate (Laboratoires SERB, Paris, France) and hepatocytes were maintained in this medium. To induce steatosis in normal hepatocytes, PHH were incubated with free fatty acid (FFA) mixtures of oleic acid and palmitic acid in a molar ratio 2:1 (500:250 μmol/L), respectively, and with 1% fatty-acid-free BSA for 48 hours.

Western Blot

Tissue samples were homogenized in NP-40 lysis buffer using a tissue grind pestle (Kimble, Rockwood, USA) or with a bead ruptor 12 (Omni International, Georgia, USA) to obtain protein lysates. Thirty μg of protein extracts from cells or tissue homogenates were separated by SDS-PAGE, transferred to polyvinylidene difluoride membrane and analyzed by immunoblotting. Membranes were probed with the following antibodies: anti-RIPK3 (#NBP1-77299; Novus, Centennial, USA) or (#AHP1797, AbD Serotec, Bio-Rad Laboratories, Hercules, USA), anti-RIPK1 (#3493; Cell Signaling, Massachusetts, USA), anti-phospho-MLKL mouse (#37333; Cell Signaling) or (#ab 196436, Abcam, Cambridge, UK), anti-phospho-AKT Ser473 (#4060; Cell Signaling), anti-AKT (#4691; Cell Signaling); anti-GAPDH (#97166; Cell Signaling) or (#sc-23233, Santa Cruz Biotechnology); anti-MLKL (#ab172868; Abcam) or (#SAB1302339, Sigma) and anti-Tubulin (#66031-1-1 g; Proteintech, Illinois, USA). All primary antibodies were used at the dilution 1:2000. As secondary antibodies, anti-rabbit-horseradish peroxidase (HRP) (#NA934V; GE healthcare, Chicago, USA) and anti-mouse-HRP (#NA931V; GE healthcare) were used. All secondary antibodies were used at the dilution 1:10 000.

Real-Time Quantitative PCR (RT-qPCR)

Total RNA was purified from liver tissue using TRIzol reagent (ThermoFisher) and a RNeasy Mini kit (Qiagen, Courtaboeuf, France). The quantity and quality of RNA were determined spectroscopically using a nanodrop (ThermoFisher). Total RNA (2 μg) was used to synthesize cDNA using the M-MLV reverse transcriptase kit (ThermoFisher) according to the manufacturer's protocol. The cDNA samples (2 μl) were used for RT-qPCR in a total volume of 10 μl using SYBR Green Reagent (Roche Diagnostics, Meylan, France) and specific primers, on a LightCycler 96 Roche Instrument. All RT-qPCRs were performed in duplicate. Data were generated and analyzed using the LightCycler 96 software 1.1.0. All values were normalized for the level of glyceraldehyde-3-phosphate dehydrogenase (GAPDH), hydroxymethylbilane synthase (Hmbs) or hypoxanthine guanine phosphoribosyltransferase (Hprt) mRNAs.

Histology and Immunohistochemistry

Paraffin sections were stained with haematoxylin and eosin (H&E), Sirius Red (SR), or incubated with various primary and secondary antibodies. Formalin-(4%) fixed and paraffin-embedded liver tissue sections were incubated in Bond Primary antibody diluent (Leica Biosystems, Wetzlar, Germany) and staining was performed on a BOND-MAX immunohistochemistry robot (Leica Biosystems) using BOND polymer refine detection solution for 3,3'-Diaminobenzidine (DAB). Anti-F4/80 antibody (Spring Bioscience, Arizona, USA), was used as primary antibody. Image acquisition was performed on a NanoZoomer S360 slide scanner (Hamamatsu Photonics, Hamamatsu, Japan). H&E and SR staining were evaluated blinded by an experienced pathologist and the histological scoring system for NAFLD was performed according to the NAS score system. Stains were quantified densitometrically (area stained per total tissue area) using FIJI software and normalized to total tissue area.

Mitochondrial Respiration Assays

The MitoTracker Red probe was used to measure the mitochondrial mass. Cells were cultured in 96-well plates, washed and incubated with MitoTracker (500 nmol/L) (ThermoFisher) in DMEM/F12, for 2 h at 37° C. A plate fluorescence reader (TECAN, Männedorf, Switzerland) was used to analyze dye fluorescence, at ex 575 nm/em 620 nm for the MitoTracker dye. The results were normalized to DAPI fluorescence. Mitochondrial respiration assays were performed using a Seahorse XF24 Cell Mito Stress Test Kit (Seahorse Biosciences, Massachusetts, USA), in accordance with manufacturer's instructions. Briefly, AML-12 cells were seeded at an optimized density of 50 000 cells per well in a 24-well Seahorse cell culture plate and incubated overnight. Each cell line was seeded in eight replicate wells (n=8). After 24 h, the Seahorse $XF^e24$ Extracellular Flux Analyzer along with $XF^e$ Wave software was used to measure the oxygen consumption rate (OCR) of each well. Successive OCR measurements were performed for each well, consisting of three basal OCR measurements, three OCR measurements following the automated injection of 1 μmol/L oligomycin, three OCR measurements following the injection of 1 μM carbonyl cyanide p-trifluoromethoxyphenyl hydrazone (FCCP), and finally three OCR measurements following the dual injection of 1 μM rotenone. Following to the OCR measurements, total cellular protein extracts were evaluated in each well for ensuring that the cell seeding was identical between control and KO cells.

Isolation of Liver Mitochondria and MRC Enzymatic Assays

Mouse liver post-nuclear supernatants were prepared by homogenizing frozen liver samples in isolation buffer (225 mM mannitol, 75 mM sucrose, 0.1 mM EDTA and 10 mM Tris-HCl pH 7.2) at a ratio of 50 mg of liver tissue per 450 μl using a mechanical bead homogenizer (RETSCH-MM301 GmbH, Verder Scientific, Haan, Germany). After centrifugation at 800 g for 10 min at 4° C., supernatants were kept, and pellets were discarded. Protein concentration was determined by the Pierce BCA Protein Assay Kit (Thermo Scientific™), using BSA as standard, and 20 μl aliquotes (2 μg/μl) were used in each assay. The activity of respiratory complexes I, II, combined II+III, IV, and citrate synthase was analyzed as described below.

The specific activity of complex I (NADH ubiquinone oxido-reductase) was determined by the decrease of NADH absorbance at 340 nm due to the oxidation of NADH. The isolated post-nuclear supernatant (40 μg) was added into 950 μl of the reaction buffer (50 mM potassium phosphate pH 7.5, 3.75 mg/mL BSA, 100 μM decylubiquinone) in two 1 mL cuvettes. Rotenone (12.5 μM) was used in one of the two cuvettes as inhibitor of complex I activity. Under the conditions of 340 nm and 37° C., the initial calibration was performed on air and cuvettes were incubated in the spectrophotometer (Beckman Coulter DU 800) for 5 min. The rate of oxidation of NADH was then measured every 15 sec during 3 min upon addition of 100 μM NADH. The specific complex I activity is the rotenone sensitive activity calculated by subtracting the rotenone insensitive activity from the total NADH ubiquinone oxido-reductase activity.

The specific activity of complex II (succinate ubiquinone oxido-reductase) was assessed by the decrease of absorbance at 600 nm due to reduction of 2,6-dichlorophenolindophenol. Liver post-nuclear supernatant (40 μg) was added into 976 μl reaction buffer (25 mM potassium phosphate pH 7.5, 20 mM succinate, 1 mM KCN, 100 μM ATP, 2 mg/mL BSA, 50 μM 2,6-dichlorophenolindophenol sodium salt) and was equilibrated for 5 min at 37° C. in each cuvette. Initial calibration was performed on air and baseline was measured every 15 sec during 3 min. The reaction was initiated following the addition of 4 μl of 25 mM decylubiquinone, kept at room temperature, and the absorbance was measured at 600 nm every 15 sec during 3 min at 37° C.

The combined activity of complexes II+III (succinate cytochrome c oxido-reductase) was measured by the increase of absorbance at 550 nm due to the reduction of cytochrome c. Post-nuclear supernatant (40 μg) was added into 880 μl of the reaction buffer (20 mM succinate, 20 mM potassium phosphate pH 7.5, 100 μM cytochrome c, 1 mM KCN, 2 mg/mL BSA, 100 μM ATP) and was equilibrated for 5 min at 37° C. Initial calibration was performed on air and baseline was measured at 550 nm every 15 sec during 3 min. The reaction was initiated following the addition of 100 μl of 1 mM cytochrome c, kept at room temperature, and the absorbance was measured at 550 nm every 20 sec during 3 min at 37° C.

The specific activity of complex IV (cytochrome c oxidase) was measured by the decrease of absorbance at 550 nm due to oxidization of reduced cytochrome c. The initial cytochrome c solution was prepared by using 100 μM reduced cytochrome c in 50 mM potassium phosphate pH 7.0. The 100% oxidized and reduced solutions of cytochrome c were respectively prepared with few grains of potassium ferricyanide and sodium dithionite in a 1 mL cuvette using initial cytochrome c solution. Absorbance of the 100% oxidized solution was measured at 550 nm after having obtained a blank on air, and then the 100% reduced solution was measured after re-blanking with the 100% oxidized solution. Aliquots of 100% reduced solution were added gradually on initial cytochrome c solution until reaching absorbances of 90-95% of the reduced solution absorbance. Then, 980 μl reduced initial solution of cytochrome c was incubated in 1 mL cuvette for 5 min at 37° C. Initial calibration was performed on air. The reaction was initiated by adding post-nuclear supernatant (40 μg) and the absorbance was measured at 550 nm every 10 sec during 3 min at 37° C.

The activity of citrate synthase (CS) was assessed by alterations of thionitrobenzoate anion formation. Liver post-nuclear supernatant (40 μg) was added to 930 μl of reaction buffer (100 mM Tris/HCl pH 8.1, 100 μM 5,5'-dithiobis-2-nitrobenzoate, 300 μtM acetyl-CoA, 500 μM oxaloacetate and 0.1% Triton X100). The absorbance was then measured at 412 nm every 20 sec during 4 min at 37° C.

All measured activities were expressed as nmol/min/mg of proteins.

Cell Proliferation Assays

AML-12 cells (5000 per well) were seeded in a 96-well plate and incubated overnight at 37° C. in DMEM/F12 Medium (ThermoFisher) supplemented with 10% fetal bovine serum (Eurobio). Cell proliferation was measured by either a BrdU colorimetric ELISA assay (Roche Diagnostics, Meylan, France) at 0, 2, 4, 8, 12 and 24 h after seeding or xCELLigence real-time cell analysis according to the manufacturer's instructions.

Cell Viability Assay

Cell viability was determined by using 3-(4,5-dimethylthiazol-2-yl)-5-(3-carboxymethoxy-phenyl)-2-(4-sulfophenyl)-2H-tetrazolium (MTT) colorimetric assay (ThermoFisher), which measures cell metabolic activity. It is based on the ability of nicotinamide adenine dinucleotide phosphate (NADPH) to reduce the MTT to its insoluble formazan end product, which has a purple color. Cells were incubated with 0.5 mg/mL of MTT reagent (ThermoFisher) for 2 h. Once MTT crystals were developed and controlled under light microscopy, they were dissolved in DMSO and quantified by measuring absorbance at 540 nm.

Oil Red-O Staining, Image Processing, and Quantification

Intracellular lipids were stained by means of Oil Red-O (Sigma). Cells were washed with phosphate buffered saline (PBS) and fixed with 4% paraformaldehyde in PBS, for 10 minutes. Fixed cells were incubated with Oil Red-O solution for 30 minutes at room temperature and then with 4',6-diamidino-2-phenylindole (DAPI) (Life Technologies) for 5 minutes. Fluorescence images were viewed with IX83 Olympus microscope, acquired with Cell-Sens V1.6 and analyzed with FIJI software. Images of 8-10 different areas per condition were visualized by fluorescence microscopy using mCherry filter, followed by computer image analysis using FIJI software. Briefly, analysis was performed by threshold converting the 8-bit Red-Green-Blue image into a binary image, which consists only of pixels representing lipid droplets. For each set of experiments, one threshold for the color saturation of the lipid droplet signal, i.e. red pixels, was defined. Importantly, after separation, the binary image was manually compared with the original image for consistency and correct binary conversion. The area occupied by lipid droplets in the image is displayed by FIJI software as surface area in $\mu m^2$, and was normalized to cell number by semi-automated counting of DAPI-stained nuclei. Enlarged views of the sections are indicated by white squares.

Quantification of Intracellular Triglyceride Content

Intracellular lipids were extracted from primary human hepatocytes using hexane/isopropyl alcohol (3:2). Cells were washed and incubated with hexane/isopropyl alcohol (3:2, vol/vol) 500 μL per well in 12-well culture plates), in a shaker (80 rpm/minute) at room temperature for 60 minutes. The contents of all wells were then transferred into a glass tube for nitrogen evaporation of the organic solvent. After evaporation, lipids were resuspended in isopropyl alcohol and transferred into duplicate 96-well plates for analysis after drying. Triglycerides were measured using Infinity™ Triglyceride kit (ThermoFisher) according to manufacturer's instructions. The absorbance of each well was measured using a Tecan microplate reader (TECAN) and converted to concentration based on a standard curve. Results were normalized to the cell protein content.

Liver tissues (20-30 mg) were homogenized in 1 mL of PBS using a Tissue-Lyser Homogenizer (Qiagen) for three cycles, 30 seconds each. The homogenates were transferred to clear glass tubes (Labelians Group, Nemours, France). Homogenates were mixed with 5 mL of chloroform and methanol (2:1, vol/vol). The mixture was vortexed vigorously and incubated for 15 minutes on ice to allow separation into two phases. The lipid extracts were condensed at the bottom phase by centrifugation at 1650 g for 10 minutes at 4° C. An aliquot of the organic solvent phase was evaporated under nitrogen gas. Lipid extracts of liver tissues were dissolved in 200 μL of isopropanol with 1% Triton X-100. For the assay itself, 10 μl of triglyceride standard or of liver lipid extract was added to a 96-well plate, and 200 μL of Infinity™ triglyceride reagent (ThermoFisher) was added to the microplate. The protein concentrations in the lysates were determined via the BCA assay kit (ThermoFisher). The absorbance was measured using the Tecan Microplate Reader. Hepatic triglyceride levels were normalized to protein content.

ELISA Analyses

Protein concentrations of human RIPK1 (SEE640Hu; Could-Clone Corp., Texas, USA), human MLKL (SER645Hu; Could-Clone Corp.) and murine RIPK1 (CSB-EL019735MO; Cusabio, Texas, USA) were determined by an ELISA kit according to the manufacturer's instructions.

Example 1—RIPK1 Inhibitor Reduces Necro-Inflammatory and Fibrotic NASH Features in HFD-Fed Mice RIPA-56 is a highly potent, selective and metabolically stable RIPK1 inhibitor, able to prevent MLKL activation and MLKL-mediated cell death, as it was herein confirmed using a well-established cell model of TNFα-induced cell death, i.e., L929 cells (FIG. 1A-C). To explore the therapeutic potential of RIPK1 inhibition in NASH, RIPA-56 was tested in a HFD mouse model. Six-week-old male C57BL/6J mice were fed NCD or HFD for 16 weeks. HFD-fed mice received no additional treatment or RIPA-56, which was administered either from the beginning of HFD feeding or 12 weeks later, to mimic prophylactic and curative treatments, respectively (FIG. 2A). Western blot analyses showed that MLKL and RIPK3, the downstream targets of RIPK1, were overexpressed in the liver of HFD-fed mice compared to NCD-fed mice. In HFD-fed mice, RIPA-56 repressed their expression in both treatments, with an almost complete inhibition in the prophylactic setting (FIG. 2B). Likewise, mRNA levels of MLKL and RIPK3 were decreased in both regimens (FIG. 3). In contrast, the expression of RIPK1 was not impacted by RIPA-56 treatment (FIG. 2B and FIG. 3). The increase of serum alanine aminotransferase (ALT) in HFD-fed mice (~5-fold increase compared with NCD-fed mice) was abolished by RIPA-56 in both prophylactic and curative settings suggesting decreased tissue damage in these animals (FIG. 2C).

Histological changes of the liver in HFD-fed mice combined steatosis, inflammatory cell infiltrates and fibrosis (FIG. 2D-I). Hepatic F4/80 immunostaining confirmed macrophage infiltration in HFD-fed mice (~10-fold increase compared with NCD-fed mice), which was suppressed by RIPA-56 in both prophylactic and curative treatments (FIG. 2D-E). In keeping with this observation, the mRNA levels of F4/80 and those of Mcp-1, a potent macrophage chemoattractant, were significantly higher in the liver of HFD-fed mice than in NCD-fed mice (~3-fold higher each), and this difference disappeared following both regimens with RIPA-56 (FIG. 2F). The expression of TNFα, a major pro-inflammatory cytokine, was increased in the liver of HFD-fed mice as well (3-fold increase), but not after RIPA-56 prophylactic treatment, and markedly reduced after curative treatment (FIG. 2F). Likewise, increments in mRNA levels of other inflammatory markers such as Ccl20, Nlrp3 or Il-1b observed in the liver of HFD-fed mice, were abrogated or reduced in RIPA-56-treated mice (FIG. 4).

Sirius red staining of liver tissue sections showed that HFD-fed mice developed pericellular fibrosis (10-fold higher than NCD-fed mice), which virtually disappeared following RIPA-56 treatments (FIG. 2G-H). Collagen-1a1 (Col1a1) mRNA levels were also increased in the liver of HFD-fed mice compared to NCD-fed mice (~6-fold increase). They were no longer increased after RIPA-56 prophylactic treatment, and reduced after curative treatment (FIG. 2I).

These results conclusively demonstrated that RIPK1 contributes to the pathogenesis of NASH, and that a prophylactic treatment with the RIPK1 inhibitor RIPA-56 prevents the histologic features of NASH, whereas a curative treatment largely attenuates their intensity.

Example 2—-RIPK1 Inhibitor Reverses Steatosis and Dampens Body Weight Gain in HFD-Fed Mice HFD-fed mice developed obesity. In a prophylactic setting, when RIPA-56 treatment and HFD were started concomitantly, the mice while still obese gained significantly less body weight than untreated HFD-fed mice (~12% lower) (FIG. 5A). These mice displayed a significant decrease in fat and relative fat mass and a trend towards increased in lean and relative lean body mass compared to untreated mice under HFD (FIG. 6A-B). By contrast, in a curative setting, the delayed start of RIPA-56 after 12 weeks of HFD did not result in differences in body weight gain, fat- or lean-mass compared with untreated HFD-fed mice (FIG. 5A and FIG. 6A-B). No significant difference in food intake, spontaneous locomotor activity or respiratory exchange ratio ($VCO_2$-to-$VO_2$ ratio) was observed between HFD-fed groups (FIG. 5B-D). Yet, using indirect calorimetry, it was noted that energy expenditure was increased in HFD-fed mice, following RIPA-56 prophylactic treatment as compared to those that received RIPA-56 curative treatment or no treatment (FIG. 5E), which could have at least partly contributed to lower body weight gain in these mice. Interestingly, even though HFD-fed mice remained obese after both curative and prophylactic RIPA-56 administration, steatosis was largely reduced in both settings (FIG. 5F-H). RIPA-56 caused a marked decrease in hepatic fat content as measured by blinded histological analyses (FIG. 5F-G) and by hepatic triglyceride content (~30-40% reduction) (FIG. 5H). Collectively, these results indicated that RIPK1 inhibition improved HFD-induced hepatic steatosis.

Example 3—RIPK1 Inhibition Promotes Fat Depletion in Primary Human Steatotic Hepatocytes To test whether RIPA-56 could directly act on hepatocytes, a model of primary human steatotic hepatocytes was first used. Hepatocytes isolated from the liver of patients with NAFLD were treated after 48 hours of primary culture with RIPA-56 or vehicle (DMSO) for 24 hours. Intracellular lipid content was assessed by Oil Red-O staining and triglyceride assay (FIG. 7A-C). RIPA-56-treated steatotic hepatocytes underwent a marked decrease in intracellular lipid droplets (FIG. 7A-B) and triglyceride content (FIG. 7C). To gain insight into the underlying mechanisms, primary human hepatocytes, in which steatosis was induced by incubation with a free fatty-acid mixture (oleic acid and palmitic acid, in a molar ratio of 2:1) for 48 hours, were also used. Free fatty acid-induced lipid droplets increased by approximately 2- to 3-fold within 48 hours without affecting cell viability (FIG. 8A-D). Akin to hepatocytes isolated from steatotic liver, primary human hepatocytes in which steatosis was induced in vitro, underwent a significant decrease in intracellular lipid droplets (FIG. 7D-E) and triglyceride content (FIG. 7F) in response to RIPA-56. This coexisted with an up-regulation of CPT1A, APOB100 and MTTP expression, suggesting that increased fatty acid β-oxidation and/or triglyceride export contributed to the anti-steatotic action of RIPA-56 (FIG. 7G).

Example 4—MLKL, a Downstream Target of RIPK1, Regulates Triglyceride Content in Hepatocytes MLKL is a downstream target of RIPK1, the phosphorylation and activation of which are inhibited by RIPA-56 within hours (FIG. 1). Also, the expression of MLKL is down-regulated in the liver of HFD-fed mice after several weeks of RIPA-56 treatment (FIG. 2B and FIG. 3). Therefore, it was hypothesized that MLKL inhibition may be accountable for the fat depletion induced by RIPA-56 in steatotic hepatocytes and tested whether necrosulfonamide, a specific inhibitor of human MLKL, reduced cellular fat in human steatotic hepatocytes. FIG. 9 shows that necrosulfonamide significantly decreased intracellular lipid droplets (FIG. 9A-B) and triglyceride content (FIG. 9C), and upregulated CPT1A expression (FIG. 9D). It was also determined if MLKL ablation would reproduce the defatting effect seen in hepatocytes exposed to necrosulfonamide. Immortalized murine hepatocytes (AML-12 cell line), in which fatty acid metabolism closely resembles that of primary hepatocytes, were knocked out (KO) for MLKL using CRISPR-Cas9. Efficient KO was confirmed by western blot analysis (FIG. 9E). Following 48-hour incubation with free fatty acids, intracellular triglyceride accumulation was significantly lower in MLKL-KO cells than in controls (FIG. 9F-H). Overall, these results indicate that destabilizing the necrosome by inhibiting RIPK1 or the final executioner MLKL, or by removing MLKL, is sufficient to decrease triglyceride content in hepatocytes. Thus, the RIPK1/MLKL axis appears to be a major pathway of hepatic lipid accumulation in NAFLD.

Example 5—MLKL Regulates Mitochondrial Biomass and Activity

To gain further insight into the mechanisms whereby the RIPK1/MLKL axis controls fat storage in hepatocytes, mitochondrial activity in MLKL-KO cells was examined. MLKL-KO cells exhibited an apparent increase in viability, as assessed by the MTT assay (FIG. 10A). This effect was independent of proliferation, which was not different between KO and control cells, as shown by BrdU assay (FIG. 10B) and xCELLigence real-time cell analysis (FIG. 10C). MTT is reduced in metabolically active cells, in part by the action of the mitochondrial dehydrogenase enzyme. The mitochondrial mass was measured and it was found a moderate but significant increase in KO cells, as compared to controls (FIG. 10D). Likewise, the mRNA levels of Pgc1a, a master regulator of mitochondrial biogenesis, were significantly increased in KO cells (FIG. 10E). Based on these findings, it was anticipated that the mitochondrial activity would be increased in KO cell line. The expression of genes involved in fatty acid β-oxidation (Cpt1a, Acox1) was measured and it was found that they were overexpressed in KO cells, compared to controls (FIG. 10E). The bioenergetic status of these cells were compared and mitochondrial respiration tests were performed. MLKL-KO cells had a markedly higher basal mitochondrial respiration than control cells (FIG. 10F-G). To distinguish oxygen consumption devoted to ATP synthesis from that due to the natural proton leak across the inner mitochondrial membrane, the ATP synthase inhibitor oligomycin was added and it showed that ATP-linked respiration was increased in KO cells (FIG. 10F-G). The addition of the accelerator ionophore FCCP, which leads to a rapid consumption of oxygen without the generation of ATP, showed that KO cells had a markedly higher maximum respiratory rate than control cells (FIG. 10F-G). Finally, it was assessed whether RIPK3-KO mice with NASH induced by a cholinedeficient, amino acid-defined (CDAA) diet, would also display improved mitochondrial bioenergetics as compared with WT mice (FIG. 11A-C). First, it was found that RIPK3-KO mice had significantly lower levels of phosphorylated MLKL (p-MLKL) compared with WT mice fed the same diet (FIG. 11A). Along with MLKL decreased activation, activities of citrate synthase (CS) and mitochondrial respiratory chain (MRC) complexes in liver mitochondria, particularly the complex II+III, were significantly enhanced in RIPK3-KO mice compared with WT mice (FIG. 11B). These differences between WT and KO mice were even more profound after a longer feeding period (FIG. 11B). Likewise, the mRNA levels of Pgc1a and Acox1 were both significantly increased in RIPK3-KO mice compared with WT mice at 32 weeks (FIG. 11C). Collectively, these results point to a novel function of MLKL activation through the regulation of mitochondrial respiration.

Example 6—RIPK1 and MLKL are Increased in the Serum of Patients with NASH

The serum concentrations of proteins mediating necroptosis were previously found to be elevated in patients with tissue injury caused by sepsis, raising the possibility that this may also occur in patients with NAFLD, as a result of necro-inflammatory activity. The serum concentrations of RIPK1 and MLKL proteins were measured in 35 patients with NAFLD, and it was found that their concentration was markedly increased in the serum of patients with active disease (histological activity score ≥2 vs. <2) (Table 1 and FIG. 12A-B). The serum concentration of both proteins was positively correlated with ALT (FIG. 12C-D). To confirm that mediators of necroptosis might be released in the extracellular milieu during necroptosis, it was tested whether L929 cells exposed to TNFα, released RIPK1 in their supernatant. It was found that RIPK1 was released in the supernatant of L929 cells exposed to TNFα, notably in the presence of Zvad, but remained undetectable, when necroptosis was abrogated by RIPA-56 or Nec-1 treatment of the cells (FIG. 12E). Altogether, these results suggest that necroptosis contributes to the pathogenesis of NAFLD, and that the release of RIPK1 and MLKL into the systemic circulation, reflects necro-inflammatory activity in human NAFLD.

TABLE 1

Characteristics of the NAFLD study population.

| Parameters | Group I (n = 8) | Group II (n = 27) |
|---|---|---|
| Age (years) | 56.4 ± 8.4 | 60.6 ± 6.2 |
| Gender (M:F) | 6:2 | 13:14 |
| Weight (kg) | 90.5 ± 9.6 | 83.7 ± 11.7 |
| BMI (kg/m$^2$) | 30.2 ± 2.4 | 29.6 ± 3.4 |
| ALT (IU/L) | 31.0 ± 5.8 | 54.8 ± 16.0*** |
| AST (IU/L) | 27.3 ± 4.3 | 40.9 ± 8.9** |
| Bilirubin (mmol/L) | 9.2 ± 1.2 | 11.1 ± 3.9 |
| ALP (IU/L) | 60.4 ± 16.5 | 69.9 ± 11.4 |
| gGT (IU/L) | 58.5 ± 42.8 | 68.0 ± 27.0 |
| Creatinine (∞mol/L) | 68.4 ± 15.9 | 75.5 ± 13.0 |
| HBA1c (%) | 6.1 ± 0.5 | 6.5 ± 0.9 |
| Cholesterol (mmol/L) | 4.7 ± 1.0 | 4.7 ± 0.6 |
| HDL (mmol/L) | 1.4 ± 0.2 | 1.1 ± 0.2 |
| LDL (mmol/L) | 2.6 ± 0.5 | 3.2 ± 0.6 |
| Triglyceride (mmol/L) | 1.0 ± 0.3 | 1.7 ± 0.6 |
| Apo A (g/L) | 1.4 ± 0.2 | 1.6 ± 0.2 |

Data are shown as mean ± SEM;

**$p < 0.01$;

***$p < 0.001$;

M, Male; F, Female; BMI, body mass index; ALT, alanine aminotransferase; AST, aspartate aminotransferase; ALP, phosphatase alkaline; gGT, gamma glutamyl transpeptidase; HBA1c, glycated haemoglobin; Apo A, apolipoprotein A. Group I: NAFLD patients with an inflammatory score < 2; Group II: NAFLD patients with an inflammatory score score ≥ 2.

The invention claimed is:

1. A method for preventing and/or treating non-alcoholic fatty liver disease (NAFLD), the method comprising administering, to a patient in need thereof, an effective amount of a compound of formula (I):

(I)

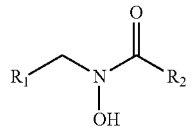

wherein:

$R_1$ is phenyl, $R_2$ is 1,1-dimethylpropyl, or a pharmaceutically acceptable salt or hydrate thereof.

2. The method of claim 1, wherein the method is a method for preventing and/or treating non-alcoholic hepatic steatosis or non-alcoholic steatohepatitis (NASH).

3. The method of claim 1, wherein said compound is:

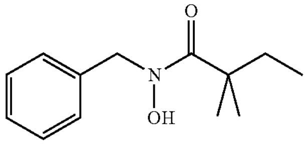 [SMILES: CCC(C)(C)C(=O)N(O)Cc1ccccc1]

(N-Benzyl-N-hydroxy-2,2-dimethylbutanamide or "RIP A-56")

or a pharmaceutically acceptable salt or hydrate thereof.

4. The method of claim 1, wherein said compound is administered by enteral or parenteral route.

5. The method of claim 1, wherein said compound is administered one or more times per day.

6. The method of claim 1, wherein the compound is administered to a patient at a regimen of 1 to 1000 mg per kg.

7. The method of claim 6, wherein the compound is administered to a patient at a regimen of 50 to 500 mg per kg.

8. The method of claim 6, wherein the compound is administered to a patient at a regimen of from 100 to 300 mg per kg.

* * * * *